(12) United States Patent
McCaffrey et al.

(10) Patent No.: US 10,194,812 B2
(45) Date of Patent: Feb. 5, 2019

(54) SYSTEM AND METHOD OF INTEGRATING A FRACTIONAL FLOW RESERVE DEVICE WITH A CONVENTIONAL HEMODYNAMIC MONITORING SYSTEM

(71) Applicant: Medtronic Vascular, Inc., Santa Rosa, CA (US)

(72) Inventors: Gerry McCaffrey, Ballybrit (IE); Fiachra Sweeney, Ballybrit (IE); Barry O'Connell, Ballybrit (IE); Christopher Murphy, Ballybrit (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 876 days.

(21) Appl. No.: 14/568,466

(22) Filed: Dec. 12, 2014

(65) Prior Publication Data

US 2016/0166158 A1 Jun. 16, 2016

(51) Int. Cl.
*A61B 5/0215* (2006.01)
*A61B 5/02* (2006.01)
(Continued)

(52) U.S. Cl.
CPC .......... *A61B 5/0215* (2013.01); *A61B 5/0004* (2013.01); *A61B 5/026* (2013.01);
(Continued)

(58) Field of Classification Search
CPC ..... A61B 5/0215; A61B 5/0004; A61B 5/026; A61B 5/742; A61B 5/7278; A61B 5/02028; A61B 5/02007; A61M 2025/0002
See application file for complete search history.

(56) References Cited

U.S. PATENT DOCUMENTS 4,718,425 A 1/1988 Tanaka et al.
4,771,782 A 9/1988 Millar
(Continued)

FOREIGN PATENT DOCUMENTS

DE 102008045878 3/2010
EP 0263190 10/1986
(Continued)

OTHER PUBLICATIONS

PCT/US2015/062866, The International Search Report and the Written Opinion, dated Mar. 22, 2016.

*Primary Examiner* — Tiffany Weston
*Assistant Examiner* — Tho Tran
(74) *Attorney, Agent, or Firm* — Medler Ferro Woodhouse & Mills PLLC

(57) ABSTRACT

A processing system received data from a Fractional Flow Reserve device and communicates data to a conventional hemodynamic monitoring system having pressure displays. The processing system receives proximal pressure measurement signal from an aortic pressure measurement device and a distal pressure measurement signal from a distal pressure measurement device. A processor computes an FFR ratio from the proximal pressure measurement signal and the distal pressure measurement signal, and converts FFR ratio to a pressure format such that the FFR ratio reads on the conventional hemodynamic monitoring system as a pressure in units of pressure. The processing system transmits the proximal pressure measurement signal, the distal pressure measurement signal, and the FFR ratio in pressure format to the conventional hemodynamic monitoring system.

20 Claims, 14 Drawing Sheets

(51) Int. Cl.
*A61B 5/00* (2006.01)
*A61B 5/026* (2006.01)
*A61M 25/00* (2006.01)

(52) U.S. Cl.
CPC ...... *A61B 5/02007* (2013.01); *A61B 5/02028* (2013.01); *A61B 5/7278* (2013.01); *A61B 5/742* (2013.01); *A61M 2025/0002* (2013.01)

(56) References Cited

U.S. PATENT DOCUMENTS

| | | |
|---|---|---|
| 4,796,641 A | 1/1989 | Mills |
| 4,815,472 A | 3/1989 | Wise |
| 4,850,358 A | 7/1989 | Millar |
| 4,901,731 A | 2/1990 | Millar |
| 4,924,877 A | 5/1990 | Brooks |
| 4,928,693 A | 5/1990 | Goodin |
| 4,936,310 A | 6/1990 | Engstrom et al. |
| 4,941,473 A | 7/1990 | Tenerz et al. |
| 4,966,148 A | 10/1990 | Millar |
| 4,966,156 A | 10/1990 | Perry et al. |
| 5,029,585 A | 7/1991 | Lieber et al. |
| 5,046,497 A | 9/1991 | Millar |
| 5,050,297 A | 9/1991 | Metzger |
| 5,085,223 A | 2/1992 | Lars et al. |
| 5,125,058 A | 6/1992 | Tenerz et al. |
| 5,195,375 A | 3/1993 | Tenerz et al. |
| 5,267,958 A | 12/1993 | Buchbinder et al. |
| 5,280,786 A | 1/1994 | Wlodarczyk et al. |
| 5,427,114 A | 6/1995 | Colliver et al. |
| 5,451,233 A | 9/1995 | Yock |
| 5,466,222 A | 11/1995 | Ressemann et al. |
| 5,526,820 A | 6/1996 | Khoury |
| 5,542,434 A | 8/1996 | Imran et al. |
| 5,564,425 A | 10/1996 | Tonokura |
| 5,569,219 A | 10/1996 | Hakki et al. |
| 5,573,007 A | 11/1996 | Bobo, Sr. |
| 5,591,129 A | 1/1997 | Shoup et al. |
| 5,637,091 A | 6/1997 | Hakky et al. |
| RE35,648 E | 11/1997 | Tenerz et al. |
| 5,694,946 A | 12/1997 | Tenerz et al. |
| 5,701,905 A | 12/1997 | Esch |
| 5,715,827 A | 2/1998 | Corl et al. |
| 5,813,997 A | 9/1998 | Imran et al. |
| 5,827,243 A | 10/1998 | Palestrant |
| 5,873,835 A | 2/1999 | Hastings |
| 5,902,248 A | 5/1999 | Millar et al. |
| 5,964,714 A | 10/1999 | Lafontaine |
| 6,033,366 A | 3/2000 | Brockway |
| 6,056,719 A | 5/2000 | Mickley |
| 6,089,103 A | 7/2000 | Smith |
| 6,106,476 A | 8/2000 | Corl et al. |
| 6,106,486 A | 8/2000 | Tenerz et al. |
| 6,112,598 A | 9/2000 | Tenerz et al. |
| 6,142,958 A | 11/2000 | Hammarstrom et al. |
| 6,167,763 B1 | 1/2001 | Tenerz et al. |
| 6,179,856 B1 | 1/2001 | Barbere |
| 6,182,513 B1 | 2/2001 | Stemme et al. |
| 6,193,669 B1 | 2/2001 | Degany |
| 6,224,585 B1 | 5/2001 | Pfeiffer |
| 6,248,083 B1 | 6/2001 | Smith et al. |
| 6,296,615 B1 | 10/2001 | Brockway et al. |
| 6,312,380 B1 | 10/2001 | Brockway et al. |
| 6,336,906 B1 | 1/2002 | Hammarstrom et al. |
| 6,354,999 B1 | 3/2002 | Dgany |
| 6,379,308 B1 | 4/2002 | Brockway |
| 6,394,986 B1 | 5/2002 | Millar |
| 6,409,677 B1 | 6/2002 | Tulkki |
| 6,471,656 B1 | 10/2002 | Shalman et al. |
| 6,517,481 B2 | 2/2003 | Hoek et al. |
| 6,546,804 B2 | 4/2003 | Stemme et al. |
| 6,551,250 B2 | 4/2003 | Khalil |
| 6,565,514 B2 | 5/2003 | Svanerudh et al. |
| 6,585,660 B2 | 7/2003 | Dorando et al. |
| 6,615,067 B2 | 9/2003 | Hoek et al. |
| 6,615,667 B2 | 9/2003 | Smith |
| 6,659,957 B1 | 12/2003 | Vardi et al. |
| 6,659,959 B2 | 12/2003 | Brockway et al. |
| 6,663,570 B2 | 12/2003 | Mott et al. |
| 6,716,178 B1 | 4/2004 | Kilpatrick et al. |
| 6,733,459 B1 | 5/2004 | Atsumi |
| 6,754,608 B2 | 6/2004 | Svanrudh et al. |
| 6,767,327 B1 | 7/2004 | Corl et al. |
| 6,821,287 B1 | 11/2004 | Jang |
| 6,860,851 B2 | 3/2005 | Knudson et al. |
| 6,868,736 B2 | 3/2005 | Sawatari et al. |
| 6,926,674 B2 | 8/2005 | Tenerz et al. |
| 6,938,474 B2 | 9/2005 | Melvas |
| 6,966,890 B2 | 11/2005 | Coyle et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,017,416 B1 | 3/2006 | Liu et al. |
| 7,021,152 B2 | 4/2006 | Tenerz |
| 7,025,727 B2 | 4/2006 | Brockway |
| 7,060,038 B2 | 6/2006 | Letort et al. |
| 7,097,620 B2 | 8/2006 | Corl et al. |
| 7,112,170 B2 | 9/2006 | Schock |
| 7,134,994 B2 | 11/2006 | Alpert et al. |
| 7,137,953 B2 | 11/2006 | Eigler et al. |
| 7,211,048 B1 | 5/2007 | Najafi |
| 7,222,539 B2 | 5/2007 | Tulkki |
| 7,229,403 B2 | 6/2007 | Schock |
| 7,245,789 B2 | 7/2007 | Bates et al. |
| 7,263,894 B2 | 9/2007 | Tenerz |
| 7,274,956 B2 | 9/2007 | Mott et al. |
| RE39,863 E | 10/2007 | Smith |
| 7,294,117 B2 | 11/2007 | Provost-tine et al. |
| 7,329,223 B1 | 2/2008 | Ainsworth et al. |
| 7,331,236 B2 | 2/2008 | Smith et al. |
| 7,343,811 B2 | 3/2008 | Tenerz et al. |
| 7,347,822 B2 | 3/2008 | Brockway |
| 7,447,388 B2 | 11/2008 | Bates et al. |
| 7,450,989 B2 | 11/2008 | Svanerudh |
| 7,454,244 B2 | 11/2008 | Kassab et al. |
| 7,458,938 B2 | 12/2008 | Patel et al. |
| 7,472,601 B1 | 1/2009 | Tenerz et al. |
| 7,481,774 B2 | 1/2009 | Brockway et al. |
| 7,527,594 B2 | 5/2009 | Vardi et al. |
| 7,532,920 B1 | 5/2009 | Ainsworth et al. |
| 7,599,588 B2 | 10/2009 | Eberle et al. |
| 7,645,233 B2 | 1/2010 | Tulkki et al. |
| 7,660,492 B2 | 2/2010 | Bates et al. |
| 7,724,148 B2 | 5/2010 | Samuelsson et al. |
| 7,731,664 B1 | 6/2010 | Millar |
| 7,775,988 B2 | 8/2010 | Pijls |
| 7,783,338 B2 | 8/2010 | Ainsworth et al. |
| 7,837,650 B1 | 11/2010 | Cox et al. |
| 7,881,573 B2 | 2/2011 | Eberle et al. |
| 7,931,603 B2 | 4/2011 | Von Malmborg et al. |
| 7,946,997 B2 | 5/2011 | Hubinette |
| 7,967,761 B2 | 6/2011 | Smith |
| 7,967,762 B2 | 6/2011 | Corl et al. |
| 7,998,089 B2 | 8/2011 | Smith |
| 8,025,623 B1 | 9/2011 | Millar |
| 8,029,447 B2 | 10/2011 | Kanz et al. |
| 8,059,923 B2 | 11/2011 | Bates et al. |
| 8,140,146 B2 | 3/2012 | Kim et al. |
| 8,157,742 B2 | 4/2012 | Taylor |
| 8,162,856 B2 | 4/2012 | Williams et al. |
| 8,174,395 B2 | 5/2012 | Samuelsson |
| 8,187,195 B2 | 5/2012 | Tulkki |
| 8,216,151 B2 | 7/2012 | Smith |
| 8,231,537 B2 | 7/2012 | Ahmed et al. |
| 8,249,815 B2 | 8/2012 | Taylor |
| 8,277,386 B2 | 10/2012 | Ahmed et al. |
| 8,282,565 B2 | 10/2012 | Mahapatra et al. |
| 8,298,156 B2 | 10/2012 | Manstrom et al. |
| 8,311,747 B2 | 11/2012 | Taylor |
| 8,311,748 B2 | 11/2012 | Taylor et al. |
| 8,311,750 B2 | 11/2012 | Taylor |
| 8,315,812 B2 | 11/2012 | Taylor |
| 8,315,813 B2 | 11/2012 | Taylor et al. |

(56) References Cited

U.S. PATENT DOCUMENTS

| | | |
|---|---|---|
| 8,315,814 B2 | 11/2012 | Taylor et al. |
| 8,317,715 B2 | 11/2012 | Belleville et al. |
| 8,320,723 B2 | 11/2012 | Eberle et al. |
| 8,321,150 B2 | 11/2012 | Taylor |
| 8,410,940 B2 | 4/2013 | Samuelsson |
| 8,419,647 B2 | 4/2013 | Corl et al. |
| 8,419,648 B2 | 4/2013 | Corl et al. |
| 8,461,997 B2 | 6/2013 | Samuelsson |
| 8,485,985 B2 | 7/2013 | Manstrom |
| 8,556,520 B2 | 10/2013 | Elenbaas et al. |
| 8,562,537 B2 | 10/2013 | Alpert et al. |
| 8,636,659 B2 | 1/2014 | Alpert et al. |
| 8,641,639 B2 | 2/2014 | Manstrom |
| 8,696,584 B2 | 4/2014 | Kassab |
| 8,698,638 B2 | 4/2014 | Samuelsson et al. |
| 8,714,021 B2 | 5/2014 | Gamage |
| 8,797,155 B2 | 8/2014 | Huennekens et al. |
| 8,857,264 B2 | 10/2014 | Gamage |
| 8,958,863 B2 | 2/2015 | Huennekens et al. |
| 8,977,336 B2 | 3/2015 | Huennekens et al. |
| 8,998,823 B2 | 4/2015 | Manstrom et al. |
| 9,011,342 B2 | 4/2015 | Manstrom et al. |
| 9,113,843 B2 | 8/2015 | Manstrom et al. |
| 9,186,072 B2 | 11/2015 | Manstrom et al. |
| 9,220,461 B2 | 12/2015 | Samuelsson et al. |
| 9,259,161 B2 | 2/2016 | Suchecki et al. |
| 9,289,137 B2 | 3/2016 | Corl |
| 9,314,584 B1 | 4/2016 | Riley et al. |
| 9,332,916 B2 | 5/2016 | Kassab |
| 9,339,348 B2 | 5/2016 | Davies et al. |
| 2001/0051769 A1 | 12/2001 | Hoek et al. |
| 2002/0013527 A1 | 1/2002 | Hoek et al. |
| 2002/0035331 A1 | 3/2002 | Brockway et al. |
| 2002/0059827 A1 | 5/2002 | Smith |
| 2002/0065472 A1 | 5/2002 | Brockway et al. |
| 2002/0072880 A1 | 6/2002 | Svanerudh et al. |
| 2002/0157473 A1 | 10/2002 | Stemme et al. |
| 2002/0173724 A1 | 11/2002 | Dorando et al. |
| 2003/0018273 A1 | 1/2003 | Corl et al. |
| 2003/0032886 A1 | 2/2003 | Dgany et al. |
| 2003/0033095 A1 | 2/2003 | Svanerudh et al. |
| 2003/0040674 A1 | 2/2003 | Cori et al. |
| 2003/0159518 A1 | 8/2003 | Sawatari et al. |
| 2003/0163052 A1 | 8/2003 | Mott et al. |
| 2003/0176850 A1 | 9/2003 | Melvas |
| 2003/0195428 A1 | 10/2003 | Brockway et al. |
| 2003/0216621 A1 | 11/2003 | Alpert et al. |
| 2004/0067000 A1 | 4/2004 | Bates et al. |
| 2004/0082844 A1 | 4/2004 | Vardi et al. |
| 2004/0082866 A1 | 4/2004 | Mott et al. |
| 2004/0116816 A1 | 6/2004 | Tenerz et al. |
| 2004/0143240 A1 | 7/2004 | Armstrong et al. |
| 2004/0143261 A1 | 7/2004 | Hartley et al. |
| 2004/0157790 A1 | 8/2004 | Herweijer et al. |
| 2004/0162548 A1 | 8/2004 | Reiser |
| 2004/0167385 A1 | 8/2004 | Rioux et al. |
| 2004/0176790 A1 | 9/2004 | Coyle |
| 2004/0230131 A1 | 11/2004 | Kassab et al. |
| 2004/0254442 A1 | 12/2004 | Williams et al. |
| 2005/0000294 A1 | 1/2005 | Tenerz et al. |
| 2005/0011272 A1 | 1/2005 | Tenerz |
| 2005/0043670 A1 | 2/2005 | Rosenberg |
| 2005/0049451 A1 | 3/2005 | Schock et al. |
| 2005/0187487 A1 | 8/2005 | Azizkhan |
| 2005/0268724 A1 | 12/2005 | Tenerz |
| 2005/0268725 A1 | 12/2005 | Tulkki |
| 2006/0005127 A1* | 1/2006 | Ferguson ............ G06F 17/218 715/248 |
| 2006/0052700 A1 | 3/2006 | Svanerudh |
| 2006/0074318 A1 | 4/2006 | Ahmed et al. |
| 2006/0094966 A1 | 5/2006 | Brockway et al. |
| 2006/0094982 A1 | 5/2006 | Corl et al. |
| 2006/0142756 A1 | 6/2006 | Davies et al. |
| 2006/0207335 A1 | 9/2006 | Tenerz et al. |
| 2006/0241505 A1 | 10/2006 | Ahmed et al. |
| 2006/0287569 A1 | 12/2006 | Schock et al. |
| 2007/0060820 A1 | 3/2007 | Lofgren et al. |
| 2007/0060822 A1 | 3/2007 | Alpert et al. |
| 2007/0078352 A1 | 4/2007 | Pijls |
| 2007/0106142 A1 | 5/2007 | Von Malmborg et al. |
| 2007/0106165 A1 | 5/2007 | Tulkki |
| 2007/0116408 A1 | 5/2007 | Eberle et al. |
| 2007/0133925 A1 | 6/2007 | Bates et al. |
| 2007/0135718 A1 | 6/2007 | Corl et al. |
| 2007/0162106 A1 | 7/2007 | Evans et al. |
| 2007/0191717 A1 | 8/2007 | Rosen et al. |
| 2007/0220986 A1 | 9/2007 | Smith et al. |
| 2007/0255144 A1 | 11/2007 | Tulkki et al. |
| 2007/0255145 A1 | 11/2007 | Smith |
| 2008/0077085 A1 | 3/2008 | Eidenschink et al. |
| 2008/0119739 A1 | 5/2008 | Vardi et al. |
| 2008/0119758 A1 | 5/2008 | Samuelsson et al. |
| 2008/0132806 A1 | 6/2008 | Smith |
| 2008/0139897 A1 | 6/2008 | Ainsworth et al. |
| 2008/0146993 A1 | 6/2008 | Krishna |
| 2008/0200770 A1 | 8/2008 | Hubinette |
| 2008/0255471 A1 | 10/2008 | Maghavi et al. |
| 2008/0262470 A1 | 10/2008 | Lee et al. |
| 2008/0269572 A1 | 10/2008 | Kanz et al. |
| 2009/0059727 A1 | 3/2009 | Bates et al. |
| 2009/0082678 A1 | 3/2009 | Smith |
| 2009/0088609 A1 | 4/2009 | Schmitz-Rode et al. |
| 2009/0088650 A1 | 4/2009 | Corl |
| 2009/0124880 A1 | 5/2009 | Smith |
| 2009/0125007 A1 | 5/2009 | Splinter |
| 2009/0248049 A1 | 10/2009 | Perkins |
| 2009/0281394 A1* | 11/2009 | Russell ............... A61B 5/0002 600/301 |
| 2010/0014810 A1 | 1/2010 | Eberle et al. |
| 2010/0087732 A1 | 4/2010 | Eberle et al. |
| 2010/0109104 A1 | 5/2010 | Tiensuu et al. |
| 2010/0113942 A1 | 5/2010 | Eberle |
| 2010/0135111 A1 | 6/2010 | Bates et al. |
| 2010/0152607 A1 | 6/2010 | Kassab |
| 2010/0234698 A1 | 9/2010 | Manstrom et al. |
| 2010/0241008 A1 | 9/2010 | Belleville et al. |
| 2010/0280330 A1 | 11/2010 | Samuelsson et al. |
| 2010/0286536 A1 | 11/2010 | Samuelsson et al. |
| 2010/0286537 A1 | 11/2010 | Pijls |
| 2011/0004198 A1 | 1/2011 | Hoch |
| 2011/0060229 A1 | 3/2011 | Hulvershorn |
| 2011/0066047 A1 | 3/2011 | Belleville et al. |
| 2011/0071407 A1* | 3/2011 | Hubinette ............ A61B 5/0002 600/485 |
| 2011/0083521 A1 | 4/2011 | Hollander et al. |
| 2011/0123154 A1 | 5/2011 | Eberle et al. |
| 2011/0137140 A1 | 6/2011 | Tearney et al. |
| 2011/0178383 A1 | 7/2011 | Kassab |
| 2011/0178413 A1 | 7/2011 | Schmitt et al. |
| 2011/0178417 A1 | 7/2011 | Kassab |
| 2011/0196255 A1 | 8/2011 | Kassab |
| 2011/0245693 A1 | 10/2011 | Hastings et al. |
| 2011/0251497 A1 | 10/2011 | Corl et al. |
| 2011/0306867 A1 | 12/2011 | Gopinathan et al. |
| 2011/0319773 A1 | 12/2011 | Kanz et al. |
| 2012/0053918 A1 | 3/2012 | Taylor |
| 2012/0071782 A1 | 3/2012 | Patil et al. |
| 2012/0072190 A1 | 3/2012 | Sharma et al. |
| 2012/0101355 A1 | 4/2012 | Gopinathan et al. |
| 2012/0101369 A1 | 4/2012 | Patil et al. |
| 2012/0108943 A1 | 5/2012 | Bates et al. |
| 2012/0136244 A1 | 5/2012 | Manstrom et al. |
| 2012/0172731 A1 | 7/2012 | Smith |
| 2012/0172732 A1 | 7/2012 | Meyer |
| 2012/0203118 A1 | 8/2012 | Samuelsson et al. |
| 2012/0220836 A1 | 8/2012 | Alpert et al. |
| 2012/0220837 A1 | 8/2012 | Alpert et al. |
| 2012/0220883 A1 | 8/2012 | Manstrom et al. |
| 2012/0227505 A1 | 9/2012 | Belleville et al. |
| 2012/0271178 A1 | 10/2012 | Smith |
| 2012/0278008 A1 | 11/2012 | Davies et al. |
| 2012/0316419 A1 | 12/2012 | Chevalier |
| 2013/0015975 A1 | 1/2013 | Huennekens et al. |
| 2013/0023762 A1 | 1/2013 | Huennekens et al. |

(56) References Cited

U.S. PATENT DOCUMENTS

| | | |
|---|---|---|
| 2013/0023763 A1 | 1/2013 | Huennekens et al. |
| 2013/0046190 A1 | 2/2013 | Davies |
| 2013/0060133 A1 | 3/2013 | Kassab et al. |
| 2013/0090555 A1 | 4/2013 | Kassab |
| 2013/0096409 A1 | 4/2013 | Hiltner et al. |
| 2013/0109980 A1 | 5/2013 | Teo |
| 2013/0116579 A1 | 5/2013 | Svanerudh |
| 2013/0131523 A1* | 5/2013 | Suchecki ............ A61B 5/02007 600/486 |
| 2013/0190633 A1 | 7/2013 | Dorando et al. |
| 2013/0216481 A1 | 8/2013 | Rosenmeier |
| 2013/0303914 A1 | 11/2013 | Hiltner et al. |
| 2013/0324864 A1 | 12/2013 | Manstrom |
| 2014/0024235 A1 | 1/2014 | Russell |
| 2014/0024950 A1 | 1/2014 | Hiltner et al. |
| 2014/0086461 A1 | 3/2014 | Yao et al. |
| 2014/0180140 A1* | 6/2014 | Alpert ................. A61B 5/0004 600/486 |
| 2014/0180141 A1 | 6/2014 | Millett |
| 2014/0187980 A1 | 7/2014 | Burkett |
| 2014/0187984 A1 | 7/2014 | Burkett |
| 2014/0276142 A1 | 9/2014 | Dorando |
| 2014/0379269 A1 | 12/2014 | Schmitt |
| 2015/0032011 A1 | 1/2015 | McGowan et al. |
| 2015/0074995 A1 | 3/2015 | Patil et al. |
| 2015/0105673 A1 | 4/2015 | Gregorich |
| 2015/0112191 A1 | 4/2015 | Gilboa et al. |
| 2015/0141853 A1 | 5/2015 | Miller et al. |
| 2015/0148693 A1 | 5/2015 | Burkett |
| 2015/0157216 A1 | 6/2015 | Stigall et al. |
| 2015/0173722 A1 | 6/2015 | Huennekens et al. |
| 2015/0223707 A1 | 8/2015 | Ludoph |
| 2015/0265167 A1 | 9/2015 | McGowan et al. |
| 2015/0272449 A1 | 10/2015 | Meyer |
| 2015/0282765 A1 | 10/2015 | Goshen et al. |
| 2015/0313479 A1 | 11/2015 | Stigall et al. |
| 2015/0359438 A1 | 12/2015 | Mccaffrey et al. |
| 2015/0359439 A1 | 12/2015 | Manstrom et al. |
| 2016/0022153 A1 | 1/2016 | Dorando |
| 2016/0022956 A1 | 1/2016 | Purdy et al. |
| 2016/0066802 A1 | 3/2016 | Keller |
| 2016/0106321 A1 | 4/2016 | Sharma et al. |

FOREIGN PATENT DOCUMENTS

| | | |
|---|---|---|
| EP | 1658808 | 8/1995 |
| EP | 1260175 | 11/2002 |
| EP | 1493381 | 1/2005 |
| EP | 1514512 | 3/2005 |
| EP | 1702641 | 9/2006 |
| EP | 01419796 B1 | 3/2008 |
| JP | 10033488 | 2/1998 |
| JP | 10137199 | 5/1998 |
| JP | 2000-333913 | 12/2000 |
| JP | 2004194996 | 7/2004 |
| JP | 2005-3638066 | 1/2005 |
| JP | 2005-095603 | 4/2005 |
| JP | 2005-3705458 | 8/2005 |
| JP | 2006-204378 | 8/2006 |
| NL | 2009285 | 8/2012 |
| WO | WO1997/000641 | 1/1997 |
| WO | WO1999/058059 | 11/1999 |
| WO | WO2003/022122 | 3/2003 |
| WO | WO2006/037082 | 4/2006 |
| WO | WO2006/117154 | 11/2006 |
| WO | WO2011/0120565 | 10/2011 |
| WO | WO2011/0161212 | 12/2011 |
| WO | WO2012093260 | 7/2012 |
| WO | WO2012173697 | 12/2012 |
| WO | WO2013061281 | 5/2013 |
| WO | WO2014/025255 | 2/2014 |
| WO | WO2014/176448 | 10/2014 |
| WO | WO2015/150128 | 10/2015 |
| WO | WO2016/001017 | 1/2016 |

* cited by examiner

SYSTEM AND METHOD OF INTEGRATING A FRACTIONAL FLOW RESERVE DEVICE WITH A CONVENTIONAL HEMODYNAMIC MONITORING SYSTEM

FIELD OF THE INVENTION

The invention methods and systems for determining a pressure gradient across a lesion of a vessel for calculating a Fractional Flow Reserve.

BACKGROUND OF THE INVENTION

The severity of a stenosis or lesion in a blood vessel may be assessed by obtaining proximal and distal pressure measurements relative to the given stenosis and using those measurements for calculating a value of the Fractional Flow Reserve (FFR). FFR is defined as the ratio of a first pressure measurement ($P_d$) taken on the distal side of the lesion to a second pressure measurement taken on the proximal side of the lesion usually within the aorta ($P_a$). Conventionally, a sensor is placed on the distal portion of a guidewire or FFR wire to obtain the first pressure measurement $P_d$, while an external pressure transducer is fluidly connected via tubing to a guide catheter for obtaining the second or aortic (AO) pressure measurement $P_a$. Calculation of the FFR value provides a lesion specific index of the functional severity of the stenosis in order to determine whether the blockage limits blood flow within the vessel to an extent that treatment is needed. An optimal or normal value of FFR in a healthy vessel is 1.00, while values less than about 0.80 are generally deemed significant and in need of an interventional treatment. Common interventional treatment options include balloon angioplasty and/or stent implantation.

Conventional FFR devices require systems to process and display information received from the FFR device. Such systems generally include a processing system to process and record information and a console or display to display information to the physician. Such processing and display systems can be expensive and need to be integrated with hospital recording systems to keep accurate medical records. The cost of these separate systems used for FFR only can be prohibitive.

FFR procedures are generally performed in a catheterization laboratory ("cath-lab") of a hospital. A catheterization laboratory is an examination room in a hospital or clinic with diagnostic imaging equipment used to visualize the arteries of the heart and the chambers of the heart and treat any stenosis or abnormality found. A typical catheterization laboratory generally includes equipment, including a hemodynamic monitoring system. Hemodynamic monitoring systems directly measure blood pressure from inside the veins, heart and arteries. They also measure blood flow and how much oxygen is in the blood. In addition, these systems have interfaces to help document diagnostic catheterizations, coronary, peripheral and electrophysiology (EP) procedures.

It would be desirable to use existing hemodynamic monitoring systems to record and display information from an FFR device, without the need for a software addition to the hemodynamic monitoring system.

BRIEF SUMMARY OF THE INVENTION

Embodiments hereof relate to a processing system for receiving data from a Fractional Flow Reserve (FFR) device and communicating data to a conventional hemodynamic monitoring system having pressure displays. The processing system includes a first data input for receiving a proximal pressure measurement ($P_A$) signal from an aortic pressure measurement device, a second data input for receiving a distal pressure measurement ($P_D$) signal from a distal pressure measurement device, a processor for computing an FFR ratio from the proximal pressure measurement signal and the distal pressure measurement signal, and an FFR converter for converting the FFR ratio to a pressure format such that the FFR ratio reads on the conventional hemodynamic monitoring system as a pressure. The FFR converter in some embodiments multiplies the FFR ratio by 100 such that the pressure format is in a similar scale as the proximal pressure measurement and the distal pressure measurement. The processing system further includes a first data output signal for transmitting the proximal pressure measurement signal to the conventional hemodynamic monitoring system, a second data output signal for transmitting the distal pressure measurement signal to the conventional hemodynamic monitoring system, and a third data output signal for transmitting the FFR ratio in the pressure format to the conventional hemodynamic monitoring system. The processing system is separate from the conventional hemodynamic monitoring system.

Embodiments hereof also relate to a method of utilizing a conventional hemodynamic monitoring system to display data during a Fractional Flow Reserve (FFR) measurement procedure. The method includes receiving a proximal pressure measurement ($P_A$) signal, receiving a distal pressure measurement ($P_D$) signal, and processing the proximal pressure measurement signal and the distal pressure measurement signal to compute an FFR ratio. The method further includes converting the FFR ratio to a pressure format such that the FFR ratio reads on the conventional hemodynamic system as a pressure. In some embodiments, the converting step includes multiplying the FFR ratio in a decimal format by 100 such that the pressure format is in a similar scale as the proximal pressure measurement and the distal pressure measurement. The method further includes transmitting the proximal pressure measurement signal, the distal pressure measurement signal, and the converted FFR ratio in the pressure format to the conventional hemodynamic monitoring system.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician when describing an object or device manipulated by the clinician. "Distal" and "distally" are positions distant from or in a direction away from the clinician. "Proximal" and "proximally" are positions near or in a direction toward the clinician. The terms "distal" and "proximal", when used with respect to a position in a vessel refer to a position or direction relative to the direction of blood flow. Accordingly, "distal" and "distally" are positions downstream of a reference position, and "proximal" and "proximally" are positions upstream of the reference position.

The following detailed description is merely exemplary in nature and is not intended to limit the invention or the application and uses of the invention. Although the description of the invention is in the context of treatment of blood vessels such as the coronary arteries, the invention may also be used in any other body passageways where it is deemed useful such as but not limited to peripheral arteries, carotid arteries, renal arteries, and/or venous applications. Furthermore, there is no intention to be bound by any expressed or implied theory presented in the preceding technical field, background, brief summary or the following detailed description.

Figure 1:
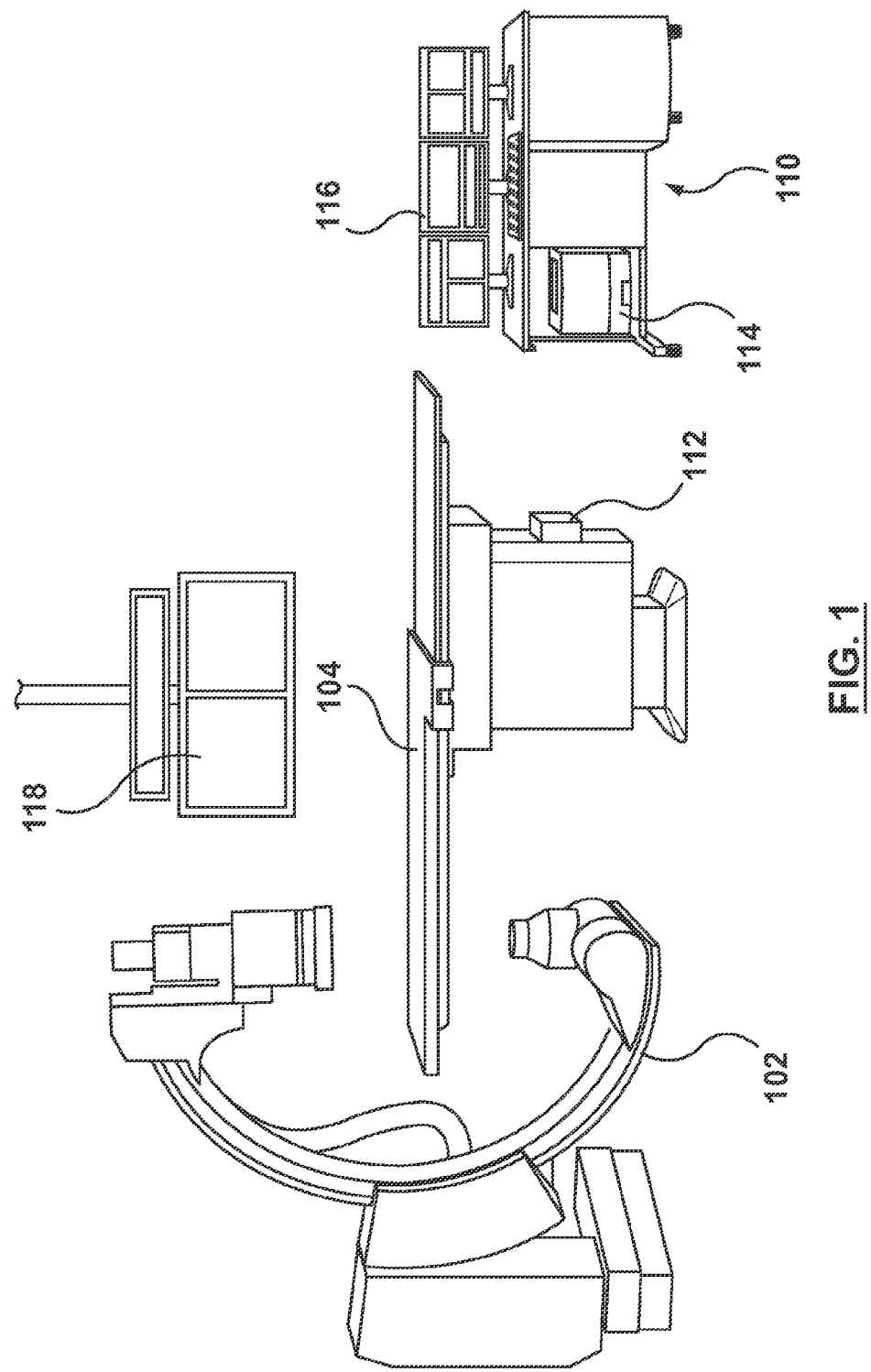
FIG. 1 is a schematic illustration of some equipment in a typical catheterization lab.

With reference to FIG. 1, a conventional catheterization laboratory generally may include, but is not limited to, a patient table 104, an imaging device 102, and a hemodynamic monitoring system 110. Hemodynamic monitoring system 110 may include, for example and not by way of limitation, a data acquisition unit 112, a processor 114, display monitors 116, and cath-lab display monitors 118, as shown in FIG. 1. Other systems and sub-systems may also be included in a catheterization laboratory.

Figure 2:
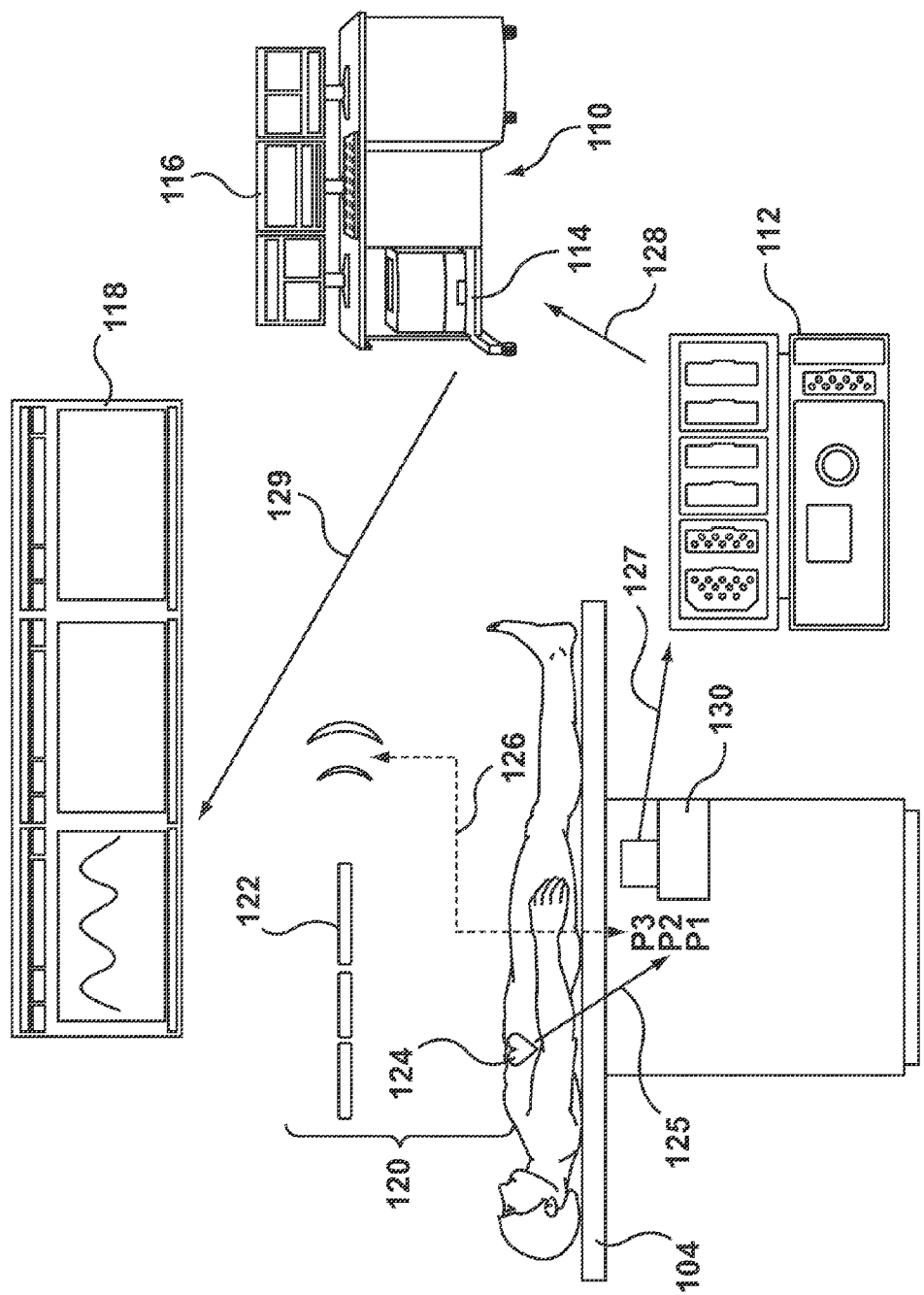
FIG. 2 is schematic illustration of selected equipment in a catheterization lab for an FFR measuring procedure including an embodiment of the processing system hereof.

FIG. 2 shows a schematic illustration of some equipment in a catheterization laboratory of FIG. 1 according to an embodiment hereof. In particular, FIG. 2 shows patient table 104, hemodynamic monitoring system 110, an FFR measurement device 120 including a distal pressure measurement device 122, a proximal or aortic pressure measurement device 124, and a processing unit 130. As in FIG. 1, hemodynamic monitoring system 110 includes a data acquisition unit 112, a processor 114, display monitors 116, and cath-lab display monitors 118. Signals from distal pressure measurement device 122 and aortic pressure measurement device 124 as sent to processing unit 130 as indicated by arrows 126, 125, respectively, and as explained in more detail below. Output signals from processing unit 130 are sent to data acquisition unit 112 of hemodynamic monitoring system 110 as indicated by arrow 127. Data acquisition unit 112 sends data to hemodynamic monitoring system 110, as indicated by arrow 128. Further, information from hemodynamic monitoring system 110 is displayed on cathlab display monitors, as indicated by arrow 129.

As explained above, hemodynamic monitoring systems 110 are conventional devices generally found in catheterization laboratories. Conventional hemodynamic monitoring systems include, but are not limited to MAC-LAB IT, XT, and XT1 available from GE Healthcare USA, McKesson Cardiology Hemo available from McKesson, Merge Hemo available from Merge Healthcare, Xper Physiomonitoring available from Phillips Healthcare, and AXIOM Sensis XP Hemo available from Siemens Healthcare. Hemodynamic monitoring system 110 is not limited to the listed examples. Data acquisition unit 112 is a data acquisition unit associated with hemodynamic monitoring system 110. Data acquisition unit 112 provides ports for attachment to cables for devices which directly measure blood pressure from inside the veins, heart and arteries, and transmit such data to processor 114 of hemodynamic monitoring system 110. For example, and not by way of limitation, the GE Healthcare MAC-LAB hemodynamic recording system may include a TRAM module data acquisition unit.

As explained above, conventional hemodynamic monitoring systems 110 are used to measure, record, and display intra-arterial blood pressure (IBP) and other properties, such as the amount of oxygen in the blood. However, conventional hemodynamic monitoring systems 110 cannot be used to measure and display FFR values during FFR procedures. Instead, either a separate system or a software upgrade to conventional systems is required. In the embodiment of FIG. 2, however, a conventional hemodynamic monitoring system 110 receives data from interface or processing unit 130 such that FFR measurements may be recorded and displayed through hemodynamic monitoring system 110 and display monitors 116, 118. Accordingly, as shown schematically in FIG. 2, processing unit 130 receives data from FFR measurement device 120. Accordingly, for the purposes of this application, the term "conventional hemodynamic monitoring system" means a hemodynamic monitoring system that does not include specific FFR recording or displaying capabilities. Accordingly, hemodynamic systems that include such FFR recording or displaying capabilities or hemodynamic systems that have had a software upgraded to include such capabilities are not "conventional hemodynamic monitoring systems.

FFR measurement device 120 can be any device or system used to measure pressures to be used to calculate FFR. As explained above, FFR measurement device 120 generally includes distal pressure measurement (also referred to as $P_d$) device 122. In some embodiments, FFR pressure measurement device may also include aortic or proximal pressure measurement (also referred to as $P_a$) device 124. However, whether aortic pressure measurement device 124 is considered part of FFR pressure measurement device 120 or is considered a separate device does not affect the present disclosure. Aortic pressure measurement device 124 generally includes a guide catheter inserted into the aorta with an external AO pressure transducer. However, other devices can be used to for measuring the aortic or proximal pressure. Distal pressure measurement device 122 may be, for example and not by way of limitation, a guidewire with a pressure sensor disposed at a distal end thereof, a catheter configured to take a pressure measurement of blood distal to the target lesion, or any other device suitable to take the distal pressure measurement. For example, and not by way of limitation, distal pressure measurement device 122 may be any of the devices described in U.S. patent application Ser. No. 14/080,433; Ser. No. 14/080,484, both filed on Nov. 14, 2013; Ser. No. 14/155,723 filed Jan. 14, 2014; and Ser. No. 14/259,896 filed Apr. 23, 2014, each of which is incorporated by reference herein in its entirety.

Figure 3:
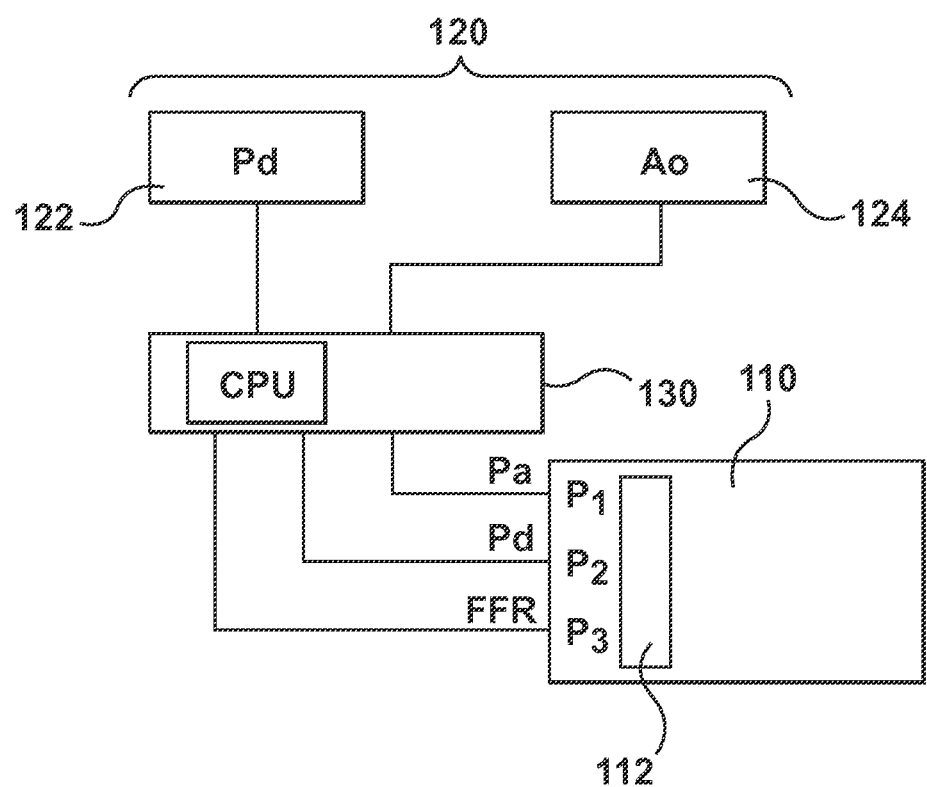
FIG. 3 is a block diagram of selected equipment of FIG. 2 including an embodiment of the processing system hereof.

FIG. 3 shows a block diagram of an embodiment of how processing unit 130 interacts with distal pressure measurement device 122, aortic pressure measurement device 124, and data acquisition unit 112 of hemodynamic monitoring system 110. In particular, processing unit 130 receives inputs from distal pressure measurement device 122 and aortic pressure measurement device 124. Processing unit 130 may receive such inputs by a cable connection to distal pressure measurement device 122 and aortic pressure measurement device 124. Alternatively, one or both of distal pressure measurement device 122 and aortic pressure measurement device 124 may include a wireless transmitter to wirelessly transmit a signal to processing unit 130, which in such an embodiment includes a wireless receiver (not shown).

After processing the data received from distal pressure measurement device 122 and aortic pressure measurement device 124, described in more detail below, processing unit 130 outputs data to data acquisition unit 112 of hemodynamic monitoring system 110. In particular, and as described in more detail below, a typical data acquisition unit 112 of hemodynamic monitoring system 110 includes at least three (3) pressure inputs or ports P1, P2, P3, as shown in FIG. 3. Pressure ports P1, P2, P3 are configured to receive data regarding blood pressure from devices typically used in catheterization laboratories, for example, and not by way of limitation, devices which measure intra-arterial blood pressure. Data acquisition unit 112 and processor 114, or, more generally, hemodynamic monitoring system 110, process the pressure data and display such pressure data on cath-lab display monitors 118. Accordingly, hemodynamic monitoring system 110 is configured to receive such pressure data from transducers in millivolts (mV) and to display such data as representative of pressure in millimeters of mercury (mmHg).

Figure 4:
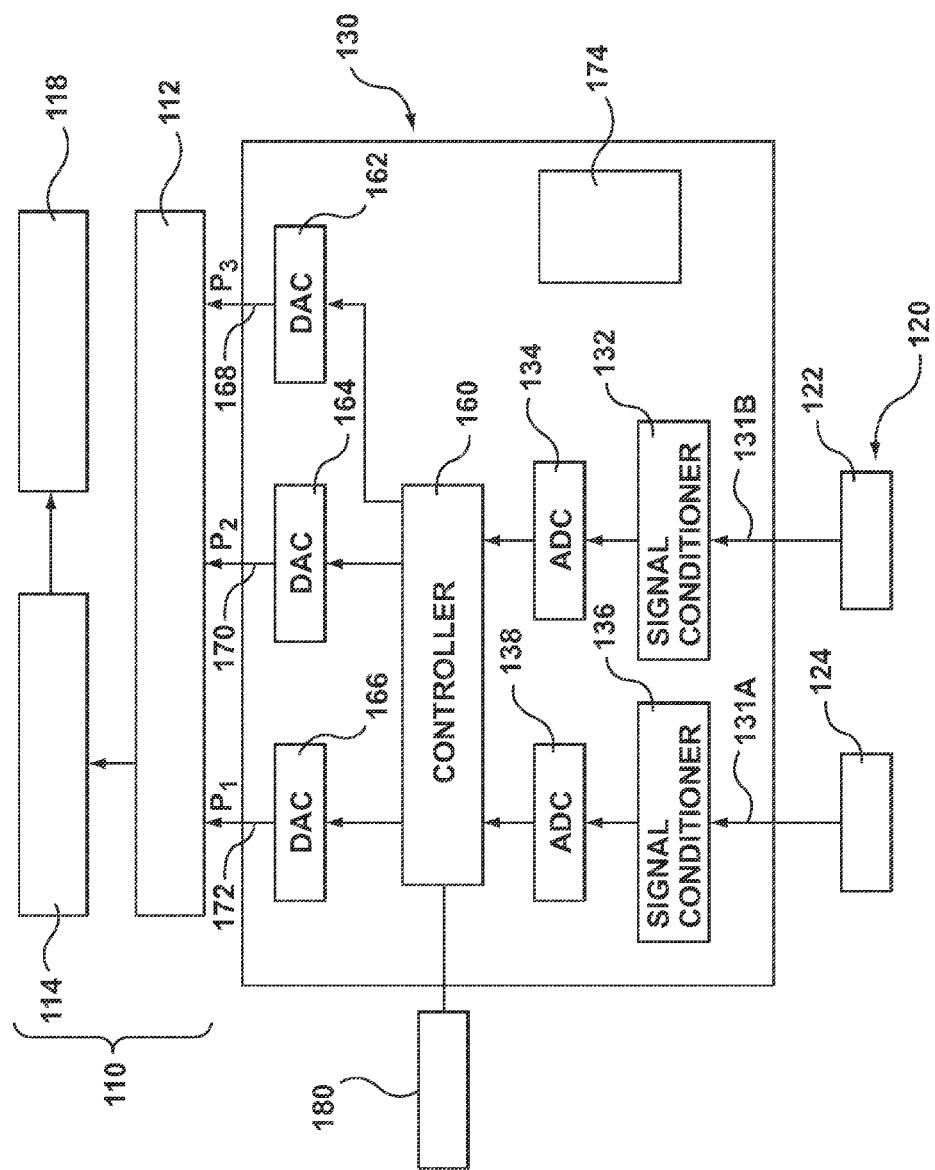
FIG. 4 is a block diagram of another embodiment of the equipment of FIG. 2 including an embodiment of the processing system hereof.
Figure 5:
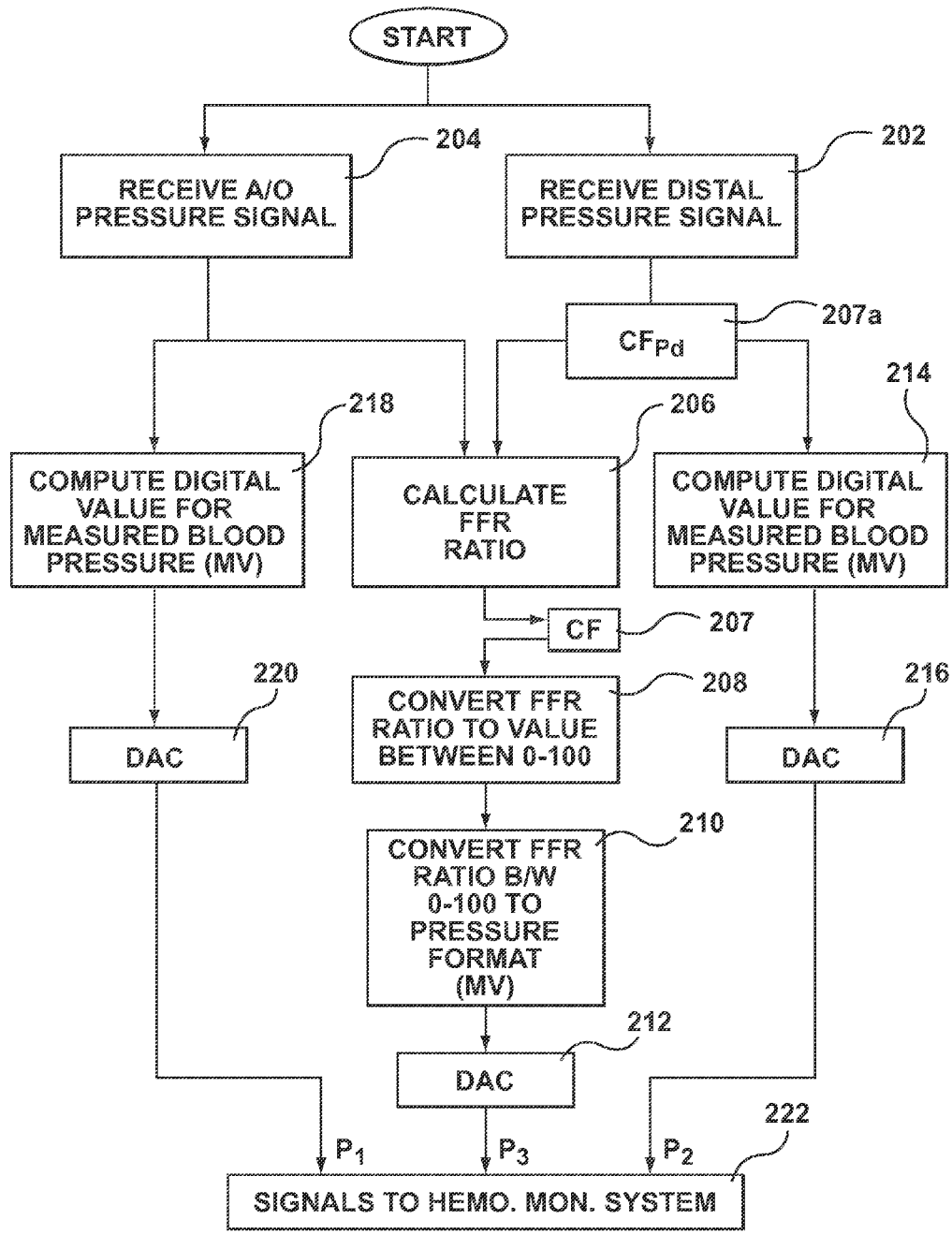
FIG. 5 is a block diagram of an embodiment of the processing system of FIG. 2.

Accordingly, FIG. 4 shows a block diagram of the main elements of a processing unit 130 using a digital approach. FIG. 5 illustrates the steps in the general operation of processing unit 130. Processing unit 130 includes a first input 131a for receiving a signal from aortic pressure measurement device 124 and a second input 131b for receiving signals from distal pressure measurement device 122. However, the specific devices from which inputs receive signals may be varied depending on the FFR measurement device 120. For example, and not by way of limitation, the distal pressure measurement device in some embodiments may also measure proximal pressure such that only a single input is needed in processing unit 130. First input 131a and second input 131b may be any input suitable for use with aortic pressure measurement device 124 and distal pressure measurement device 122. For example, and not by way of limitation, first input 131a and second input 131b may each be a receptacle, socket or port configured to receive a plug or prong at an end of a cable coupled to aortic pressure measurement device 124 and distal pressure measurement device 122, respectively. In another non-limiting example, first input 131a and/or second input 131b may be a wireless receiver configured to receive a wireless signal from aortic pressure measurement device 124 and/or distal pressure measurement device 122, respectively.

As shown in FIGS. 4 and 5, the following steps are taken by a controller 160 of processing unit 130. In particular, in step 202, controller 160 receives a signal (Pd) from distal pressure measurement device 122 through a distal pressure measurement signal conditioner 132 and an analog-to-digital converter 134. Similarly, in step 204, controller 160 receives a signal (Pa) from aortic pressure measurement device 124 through an aortic pressure measurement signal conditioner 136 and an analog-to-digital converter 138. Analog-to-digital converters 134, 138 may not be included in processing unit 130. In particular, if the signals from distal pressure measurement device 122 and/or aortic pressure measurement device are received wirelessly, such signals may be converted to digital signals before being is sent to processing unit 130. For example, and not by way of limitation, the signal from distal pressure measurement device 122 may be converted to a digital signal within FFR measurement device 120 and then sent wirelessly to processing unit 130. Signal conditioners 132, 136 may be any devices or processes used to make the signals received by processing unit suitable for processing. For example and not by way of limitation, signal conditioners 132, 136 may condition the signals from distal pressure measurement device 122 and aortic pressure measurement device 124 through amplification, filtering, converting, range matching, isolation, and other similar processes or devices.

The signal from aortic pressure aortic pressure measurement device 124 is used both to calculate Pa, as described in more detail below (steps 218, 220), and to calculate FFR (step 206). Similarly, the signal from distal pressure measurement device 122 is used both for Pd, as described in more detail below (steps 214, 216), and to calculate FFR (step 206). In step 206, controller 160 calculates the FFR ratio. As explained above, the FFR ratio is a ratio of the distal pressure in relation to the aortic pressure. Thus, FFR is calculated as $P_d$ divided by $P_a$. Accordingly, FFR is a ratio without units. Further, since the distal pressure is generally less than the aortic pressure, the FFR ratio is generally between 0.00 and 1.00, and more particularly, between 0.01 and 1.00.

Step 207 shown in FIG. 5 is an optional step of applying a correction factor to the calculated FFR. Step 207 is optional because the correction factor is not needed for a guidewire-based distal pressure measurement device. However, in some instances, with a catheter based distal pressure measurement device 122, it may be necessary to apply a correction factor to the FFR. This is due to the fact that a catheter-based distal pressure measurement device 122 may be larger in cross-section than a guidewire-based distal pressure measurement device 122. In such a situation, the larger crossing profile of the device itself may cause an obstruction and artificially increase the pressure drop across the lesion. Accordingly, in such a situation, the distal pressure measured may be lower than the distal pressure measured across the identical lesion with a guidewire-based distal pressure measurement device 122. Such an artificially lower distal pressure would also result in an artificially low FFR ratio. Thus, comparing an FFR measurement with a catheter-based distal pressure measurement device with traditional values of FFR with a guidewire-based distal pressure measurement device would result in interventional procedures for lesions that traditionally would not require intervention. Accordingly, in step 207, a correction factor CF may be applied to the calculated FFR. Such a correction factor CF is calculated using clinical data, mathematical formulas, or a combination of both. In another embodiment, the correction factor may instead be applied to the distal pressure measurement $P_d$. Applying the correction factor to the distal pressure measurement $P_d$ provides for the correct value for FFR and also provides a distal pressure $P_d$ that is consistent with the distal pressure that would have been obtained with a guidewire-based distal pressure measurement device. In such a situation, the correction factor $CF_{Pd}$ may be applied after the digital pressure signal is received but prior to calculating FFR, as indicated in step 207a of FIG. 5. If $CF_{Pd}$ is used to correct the distal pressure measurement $P_d$, the following formula would be used:

$$FFR = \frac{Pd}{Pa} \ 0.8 = \frac{80}{100} \quad (1)$$

$$FFR \times CF = CF_{FFR} \quad (2)$$

$$CF_{FFR} = \frac{CF_{Pd}}{Pa} \ 0.7 = \frac{CF_{Pd}}{100} \quad (3)$$

$$CF_{Pd} = 70 \quad (4)$$

Many conventional hemodynamic monitoring systems do not include the ability to apply a correction factor to the FFR calculation or to the distal pressure measurement $P_d$. Thus, processing system 130 as described herein provides the additional benefit of being compatible with a catheter-based distal pressure measurement device 122 without the need for costly software upgrades to conventional hemodynamic monitoring systems or the purchase of a separate system just for FFR measurements.

Figure 6:
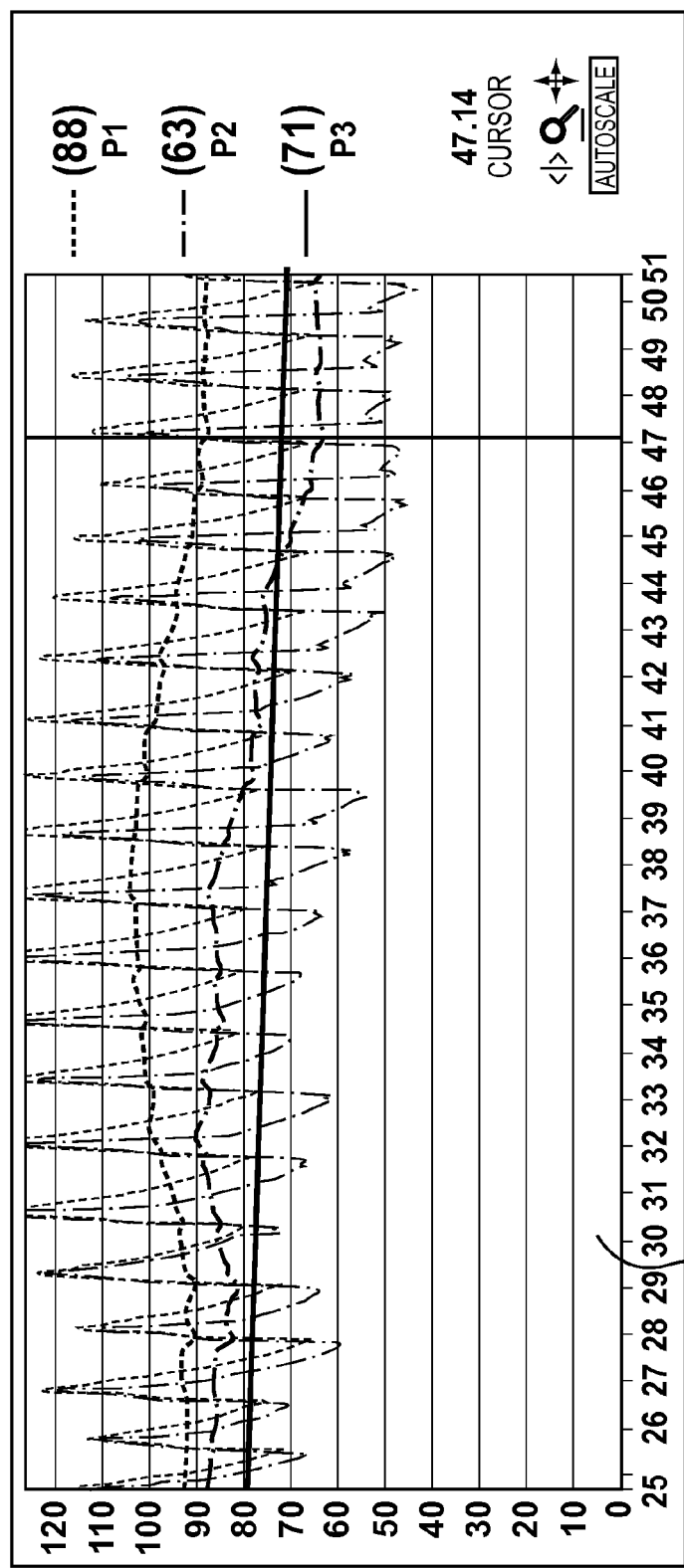
FIG. 6 is an exemplary screen shot of a cath-lab display monitor during an FFR procedure using an embodiment of the processing system hereof.

As explained in more detail below, the present application describes displaying FFR on a device configured to display blood pressure. Accordingly, in order to be meaningfully displayed, FFR should be in the same range or scale as normally observed for blood pressure. Most conventional hemodynamic recording systems do not have the ability to individually control the scale of the displays for P1, P2, and P3. In such systems, the graph displayed by cath-lab monitors 118 is generally from 0 to 120, as shown by the vertical axis in FIG. 6. However, with FFR calculated as a ratio between 0.00 and 1.00, displaying FFR on a scale of 0 to 120 would be hard to distinguish. Thus, in such cases, step 208 controller 160 converts FFR to a number from 0 to 100, although generally it will be at least 1. This is done by multiplying the FFR ratio by 100. For example, and not by way of limitation, if the aortic pressure $P_a$ is 88 mmHg and the distal pressure $P_d$ is 66 mmHg, controller 160 will calculate FFR as 0.75 in step 206. Controller 160 will further multiply 0.75 by 100 in optional step 208 such that FFR can be displayed as 75 mmHg in the same range as the aortic and distal pressures, as explained in more detail below. If FFR were displayed as 0.75, the FFR value would not be distinguishable in the graph of FFR on the cath-lab display monitors 118 due to the scale used for pressure readings, as will be apparent below. Some conventional hemodynamic recording systems allow a user to select individual scales for P1, P2, and P3. In such a situation, a scale of 0.00 to 1.00 can be used for P3 while the conventional scale of 0 to 120, as shown in FIG. 6, can be used for P1 and P2. In such a situation, step 208 is not necessary.

In step 210, the converted FFR value is converted to a "pressure format". The term "pressure format" as used herein means the format that conventional hemodynamic monitoring systems use to record and display pressures in mmHg. Thus, for example, the FFR ratio (which does not have a unit of measure) will be displayed on cath-lab monitors 118 as 75 mmHg on P3 (or 0.75 mmHg if step 208 is not utilized). Most pressure transducers in use conform to the ANSI/AAMI BP22-1994 standard for blood pressure transducers, accepting an excitation voltage of 4 to 8 VRM5 at a frequency of 0 to 5 kHz, and having a sensitivity of 5 µV/V/mmHg (5 µV output per volt of excitation voltage per mmHg of pressure), an input impedance greater than 200 ohms, an output impedance smaller than 3,000 ohms, and a zero balance within ±75 mmHg. Accordingly, the transducer aortic pressure measurement device 124 generally will conform to ANSI/AAMI BP22-1994. The transducers used in distal pressure measurement device 122 may conform to ANSI/AAMI BP22-1994, but need not. In particular, if controller 160 knows the pressure that corresponds to the signal it receives from distal pressure measurement device 122, then that is sufficient for performing the functions of controller 160. However, in order to properly communicate with hemodynamic monitoring system 110, the outputs from processing unit 130 must be in the above-referenced "pressure format", and such conventional hemodynamic monitoring systems 110 generally use this ANSI/AAMI BP22-1994. Thus, the outputs from processing unit 130 are in mV such that they can be recorded and displayed as mmHg in hemodynamic monitoring system 110. Thus, for the FFR ratio to be displayed in "pressure format", the signal sent to hemodynamic monitoring system 110 needs to be the signal that would have been produced by a pressure transducer detecting a blood pressure of the value of the converted FFR. For example, and not by way of limitation, for a transducer sensitivity of 5 µV/V/mmHg, an excitation voltage of 5 V and a pressure of 100 mmHg, a pressure transducer will output a differential voltage of (5 µV/V/mmHg)×(5 V)×(100 mmHg), or 2.5 mV. For the same combination of sensitivity, excitation voltage and pressure, the interface will also output the same differential voltage of 2.5 mV. This differential voltage can be expressed algebraically as: $V_{EXC} \times SENS \times FFR$, where $V_{EXC}$ is the root-mean-square (RMS) differential voltage across the excitation terminals, SENS is the transducer sensitivity which the hemodynamic monitoring system 140 is configured to work with, and FFR is the converted FFR value. Controller 160 also emulates the input and output impedances of a pressure transducer. In summary, in step 210, controller 160 computes the equivalent differential pressure transducer output voltage as the product of the transducer sensitivity, excitation voltage and converted FFR value, and computes an appropriate digital value that is proportional to the equivalent differential voltage.

After controller 160 has converted the FFR value to a pressure format, controller 160 sends the digital value to a digital-to-analog converter 162, as shown in FIG. 4 and step 212 in FIG. 5.

As described above, in step 202, controller 160 receives a signal from distal pressure measurement device 122 through distal pressure measurement signal conditioner 132 and analog-to-digital converter 134 (if necessary, see paragraph 0028 above). In step 214, controller 160 computes the digital value for the measured distal blood pressure. Step 214 is similar to step 210, except that instead of an FFR value, the measured distal blood pressure from distal pressure measurement device 122 is used. Controller 160 then sends this digital value to a digital-to-analog converter 164, as shown in FIG. 4 and step 216 in FIG. 5.

Similarly, and also as described above, in step 204, controller 160 receives a signal from aortic pressure measurement device 124 through aortic pressure measurement signal conditioner 136 and analog-to-digital converter 138. In step 218, controller 160 computes the digital value for the measured aortic blood pressure. Step 218 is similar to step 210, except that instead of an FFR value, the measured aortic pressure value from aortic pressure measurement device 124 is used. Controller 160 then sends this digital value to a digital-to-analog converter 166, as shown in FIG. 4 and step 220 in FIG. 5.

In step 222, the signals from digital-to-analog converters 162, 164, and 166 are sent to hemodynamic monitoring system 110. In an embodiment, the signals from digital-to-analog converters 162, 164, and 166 are sent to receptacles or ports P3, P2, and P1 of data acquisition unit 112, respectively, such as through outlets, plugs, or prongs 168, 170, and 172, as shown in FIG. 4. Data from data acquisition unit 112 is then utilized by the remainder of hemodynamic monitoring system 110, such as but not limited to, processor 114 and cath-lab display monitor 118, as shown in FIG. 4.

The resulting display on cath-lab display monitor 118 may be as depicted in FIG. 6. As can be seen in FIG. 6, the proximal or aortic pressure measurement is shown as P1, the distal pressure measurement is shown as P2, and the FFR value is shown in pressure format as mmHg as P3. A clinician viewing cath-lab display monitor 118 knows that the P3 reading of 71 mmHg in FIG. 6 means an FFR of 0.71.

Processing system 130 hereof may also include other features and devices as needed or desired. For example, and not by way of limitation, a power source 174 may be provided as part of processing system 130. Power source 174 may be a battery or a receptacle configured to receive power from another source, such as a power outlet. Other devices or features, such as but not limited to, wireless receivers and transmitters, indicators such as lights, alarms, and other similar features.

Figure 4A:
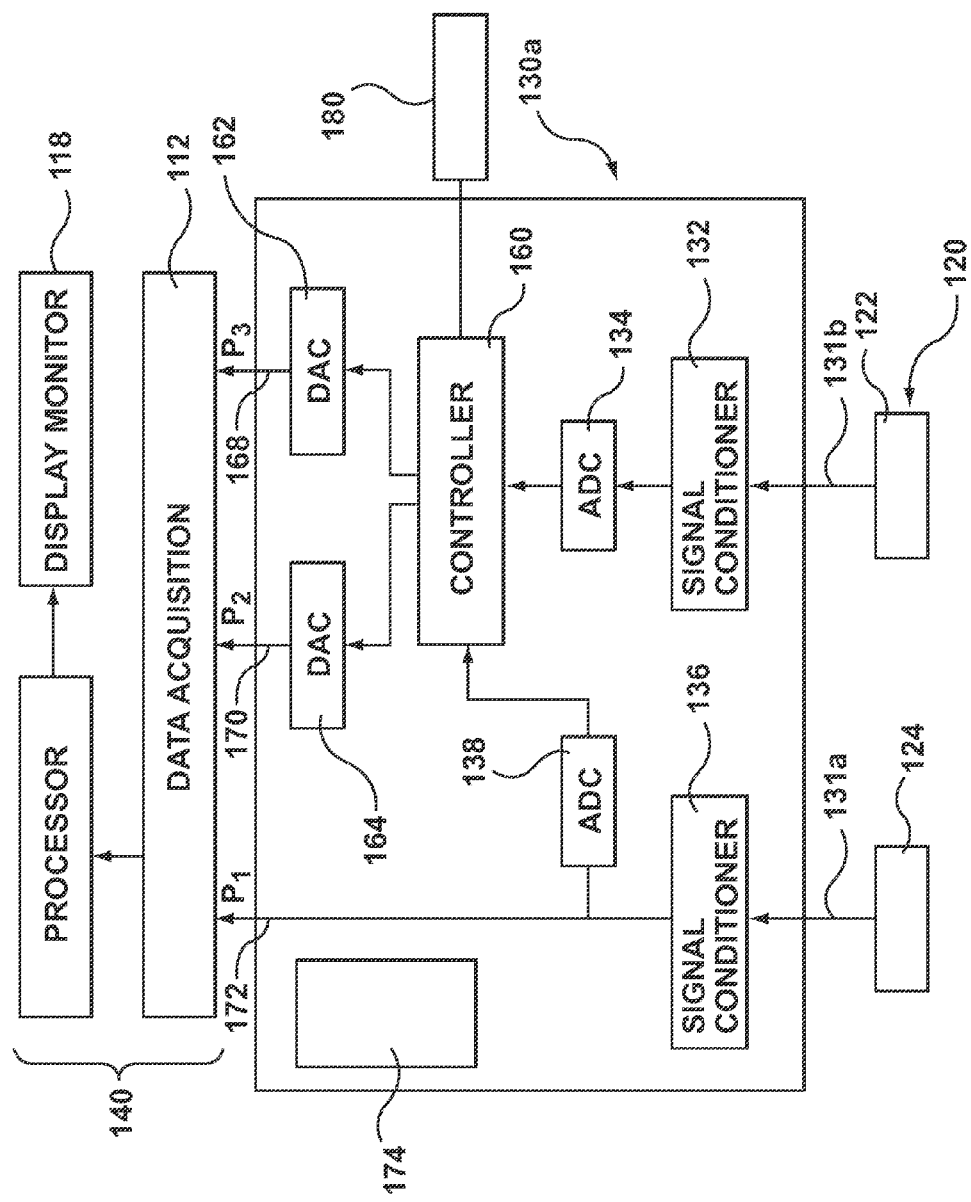
FIG. 4A is a block diagram of the equipment of FIG. 2 including another embodiment of the processing system hereof.

FIG. 4A shows a processing system 130a similar to processing system of FIG. 4. However, in processing system 130a, the aortic pressure signal from aortic pressure measurement device 124 is not converted to a digital signal and then converted back to an analog signal before being sent to port P1. Instead, second input 131b of processing unit 130 receives a signal from aortic pressure measurement device 124. The signal is conditioned by aortic pressure measurement signal conditioner 136 and is sent to receptacle or port P1 through outlet plug, or prong 172, as shown in FIG. 4A. Further, the signal is split and sent to controller 160 through analog-digital converted 138, as shown in FIG. 4A. The remainder of the processing through controller 160 and to ports P2 and P3 is as described above with respect to FIGS. 4 and 5.

Figure 7:
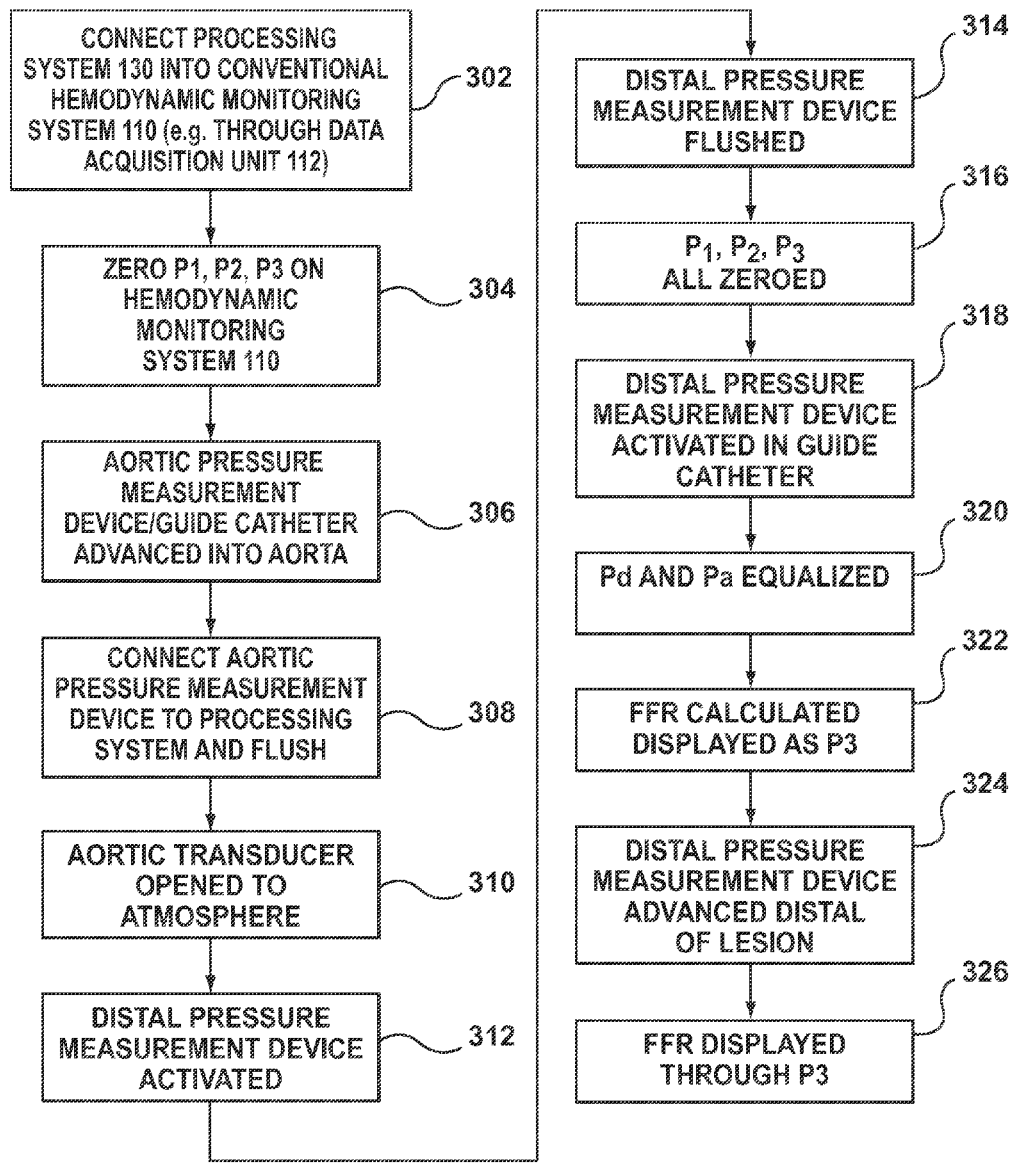
FIG. 7 is a block diagram of an embodiment of a method for preparing the systems hereof for an FFR procedure.

FIG. 7 shows an embodiment of a method of preparing and using the systems described above for an FFR procedure. In particular, in step 302, processing system 130 is connected to conventional hemodynamic monitoring system 110. In the embodiment described above, step 302 may be accomplished by connecting outlets, plugs, or prongs 168, 170, and 172 of processing system 130 to inputs P3, P2, P1 of data acquisition unit 112 of conventional hemodynamic monitoring system 110.

With processing system 130 connecting to conventional hemodynamic monitoring system 110, channels for P1, P2, P3 are "zeroed". The conventional hemodynamic monitoring system 130 may prompt the user to zero the channels. "Zeroing" the channels sets "zero" for each port P1, P2, and P3. Since processing system 130 is not yet connected to aortic pressure measurement device 124 or distal pressure measurement device 122, ports P1, P2, and P3 should be recording a pressure of zero. Step 304 sets this zero.

Step 306 is inserting aortic pressure measurement device 124 into the blood stream. As noted above, aortic pressure measurement device 124 generally includes a guide catheter (not shown) inserted into the aorta with an external AO pressure transducer. In step 306, the guide catheter is advanced through the vasculature such that the guide catheter is disposed within the aorta with a distal end thereof disposed within the aorta at an ostium of the aorta adjacent the branch vessel within which a target lesion is located. Although step 306 is shown and described prior to steps 308-314, step 306 does not necessarily need to be before steps 308-314.

Figure 8:
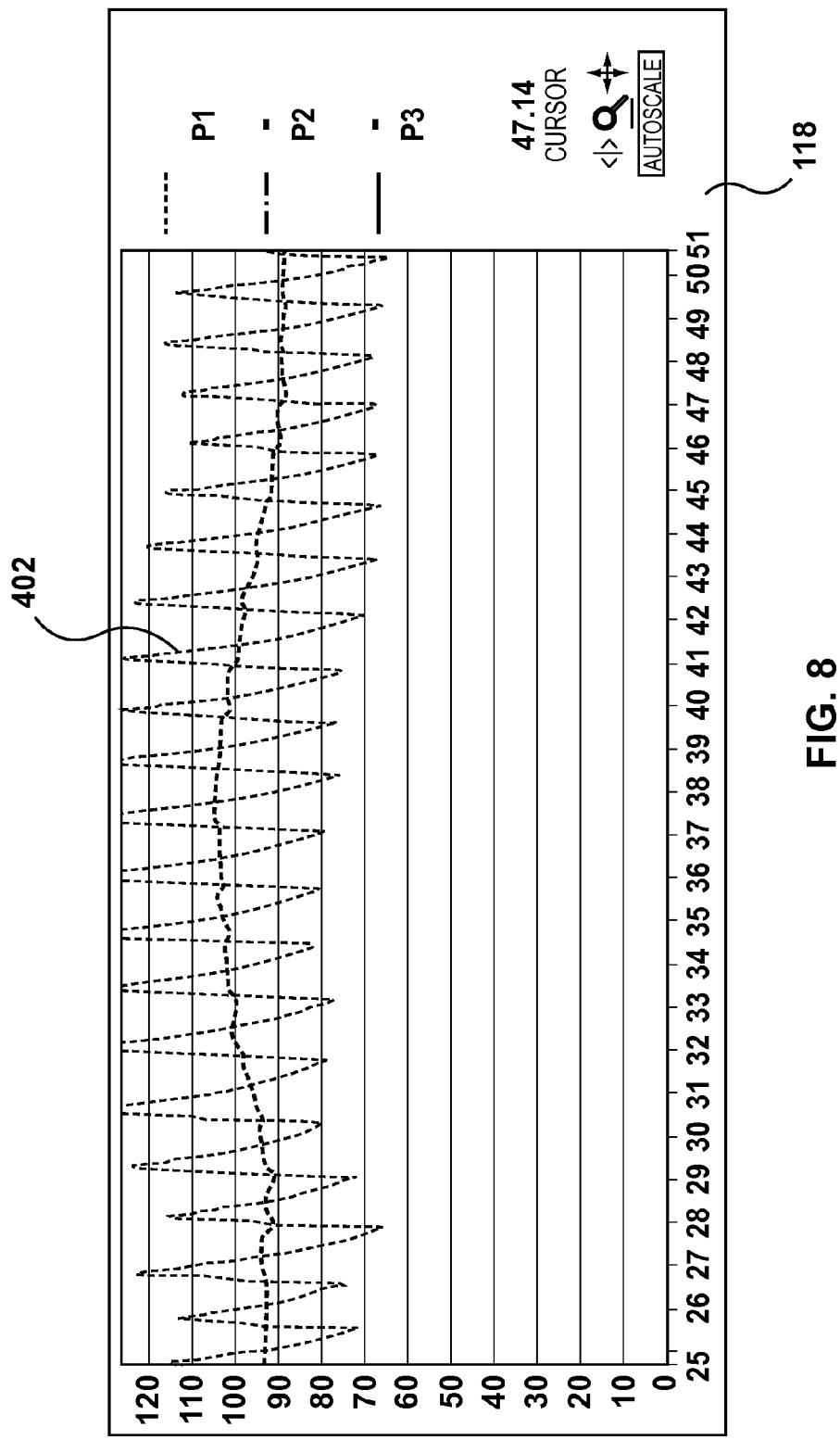
FIGS. 8-13 are an exemplary screen shots of a cath-lab display monitor during an FFR procedure using an embodiment of the processing system hereof.

In step 308, aortic pressure measurement device 124 is connected to processing system 130 and activated. As explained above, aortic pressure measurement device 124 may be connected to processing system 130 by a cable or by a wireless connection. If a wireless connection is used, the wireless connection between aortic pressure measurement device 124 and processing system 130 is made automatically when aortic pressure measurement device 124 is activated, such as by turning aortic pressure measurement device "on". With aortic pressure measurement device 124 activated, hemodynamic monitoring system 110 displays the AO pressure as trace 402 on display monitor 118 of conventional hemodynamic monitoring system 110 at port P1 through processing system 130, as shown in FIG. 8. As also described in step 306, aortic pressure measurement device 124 is flushed. Aortic pressure measurement device 124 can be flushed with saline or other fluids. Pressure wave 402 represents the pressure recorded by the external AO pressure transducer of aortic pressure measurement device 124. Distal pressure measurement device 122 is not yet connected to the system. Accordingly, ports P2 and P3 are not recording any data.

Figure 9:
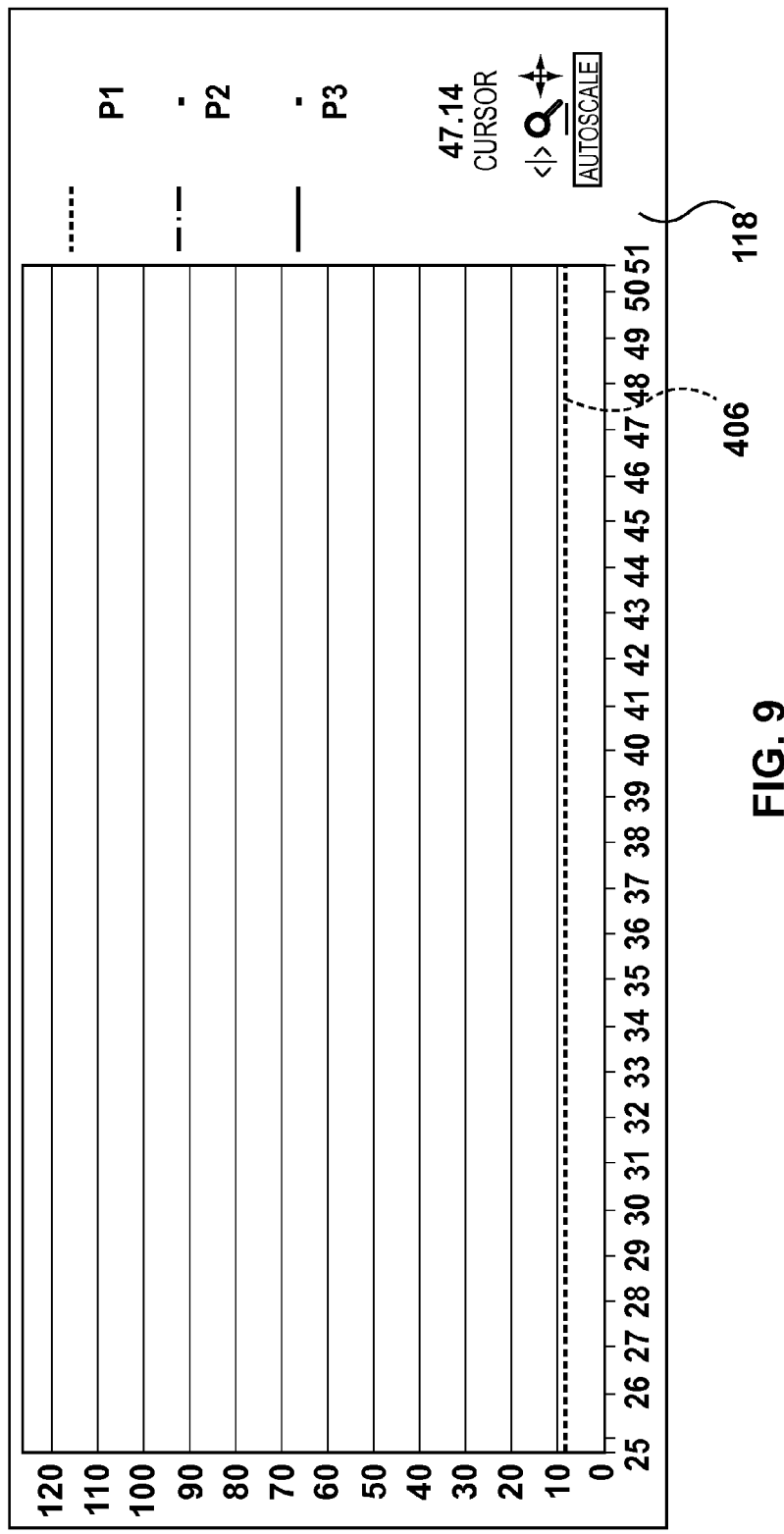

Step 310 of shown in FIG. 7 is to open the stopcock of the AO pressure transducer of aortic pressure measurement device 124. With the AO pressure transducer opened to atmosphere, the pressure recorded by port P1 connected to aortic pressure measurement device 124 drops near zero, as shown by trace 406 in FIG. 9. Trace 406 may not drop all the way to 0 mmHg because aortic pressure measurement device 124 has not yet been "zeroed".

Figure 10:
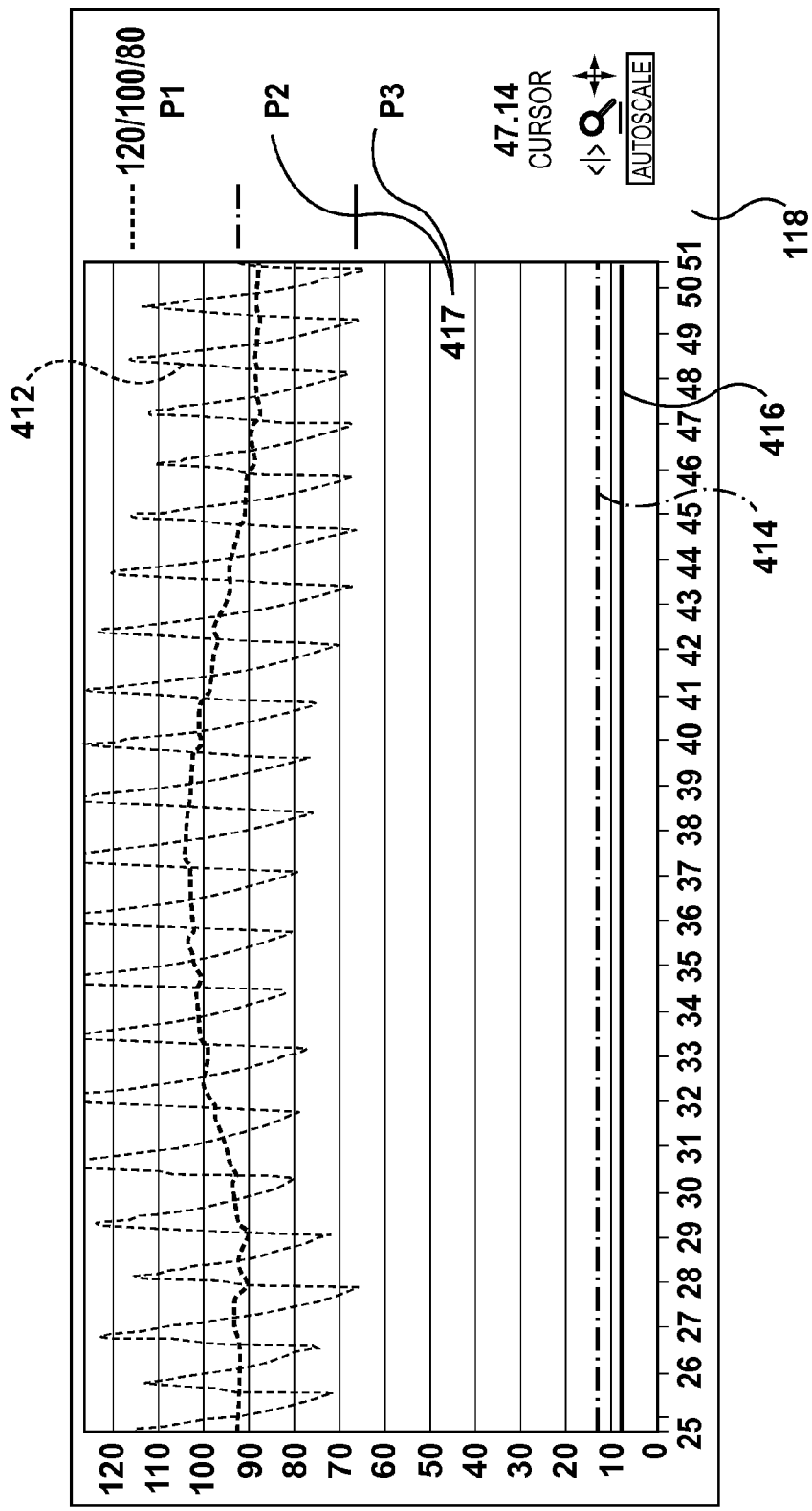

Step 312 shown in FIG. 7 is to activate distal pressure measurement device 122. Distal pressure measurement device 122 is activated while it is still outside of the body. Distal pressure measurement device 122 is also connected to processing system 130 and, because processing system 130 is connected to hemodynamic monitoring system 110, as explained above, distal pressure measurement device 122 is connected to hemodynamic monitoring system 110 through processing system 130. As explained above, distal pressure measurement device 122 may be connected to processing system 130 by a cable or by a wireless connection. If a wireless connection is used, the wireless connection between distal pressure measurement device 122 and processing system 130 is made automatically when activating distal pressure measurement device 122, such as by turning distal pressure measurement device "on". With distal pressure measurement device 122 activated and not inserted into the body, hemodynamic monitoring system 110 displays the AO pressure as trace 412, the pressure from distal pressure measurement device 122 as trace 414 through port P2, and trace 416 through port P3, as shown in FIG. 10. As explained above, port P3 is the FFR calculation converted to a pressure format. For the purposes of the example screens shown in the Figures, the FFR value has also been multiplied by 100 to put it the range from 1-100. However, as seen in FIG. 10, pressure trace 416 for port P3/FFR reads zero. This is a safety feature than may incorporated into controller 160 such that FFR is not outputted to hemodynamic system 110 until after the ports have been equalized, as explained in more detail below.

The user then flushes distal pressure measurement device 122, as shown in step 314. Distal pressure measurement device 122 can be flushed with saline or other fluids. Other steps to prepare distal pressure measurement device for insertion into the patient can also be performed, as necessary.

Figure 11:
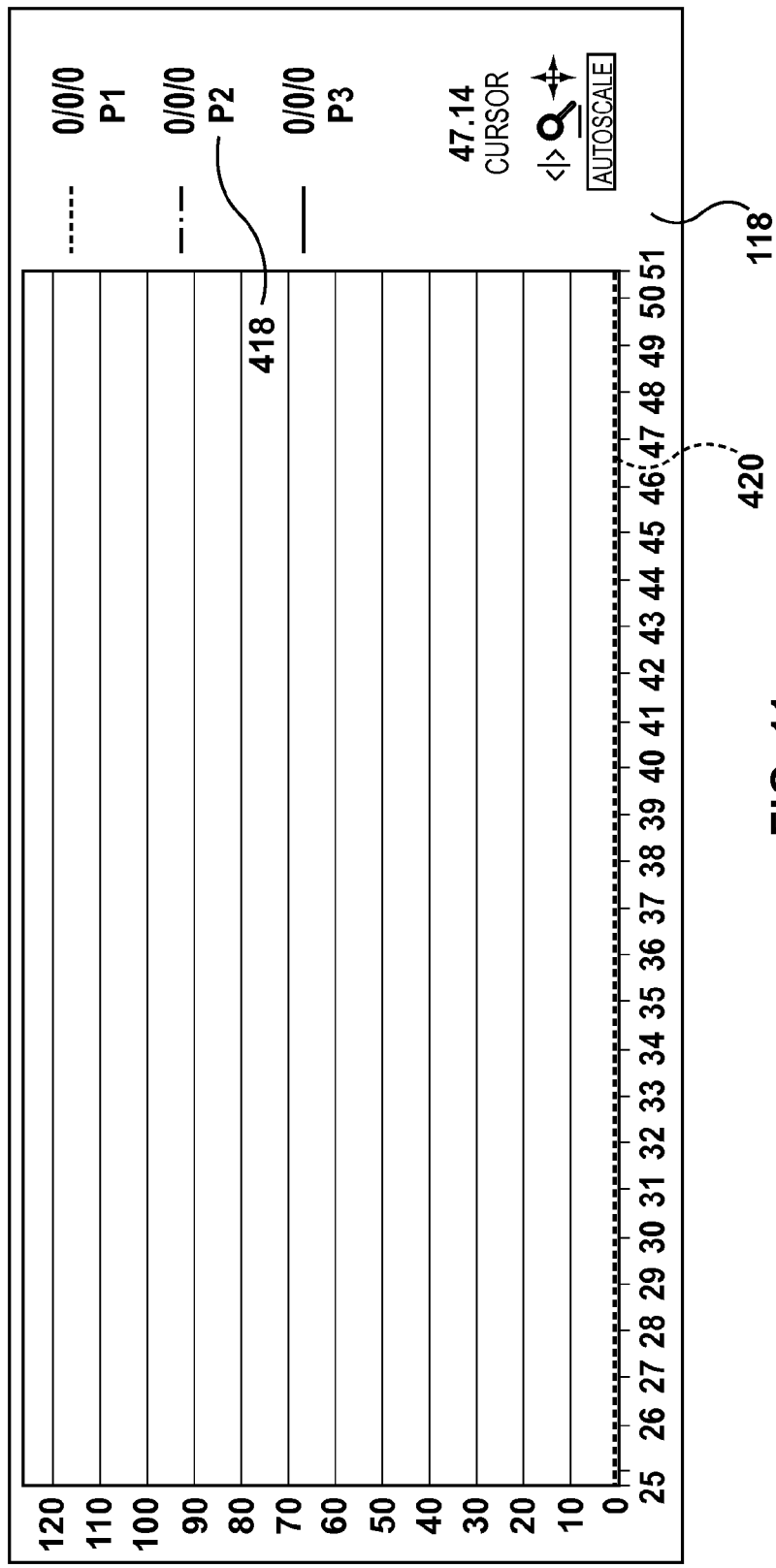

Ports P1, P2, and P3 are then "zeroed" in controller 160, as shown in step 316 of FIG. 7. To "zero" ports P1, P2, and P3, both the aortic transducer of aortic pressure measurement device 124 and distal pressure measurement device 122 are opened to atmosphere, such as by opening a stopcock of each device, as described above. Buttons or other devices on the distal pressure measurement device 122, aortic pressure measurement device 124, processing system 130, external interface 180 or other devices connected to controller 160 may be activated. "Zeroing" of the ports gives controller 160 control of the zero level for each device. Thus, the pressures for ports P1, P2, and P3 are all calibrated to zero when measuring atmospheric pressure. As shown in FIG. 11, the traces 420 for all three ports P1, P2, and P3 reflect a pressure of zero. Also, the pressures for each read zero at 418, as also shown in FIG. 11.

Figure 12:
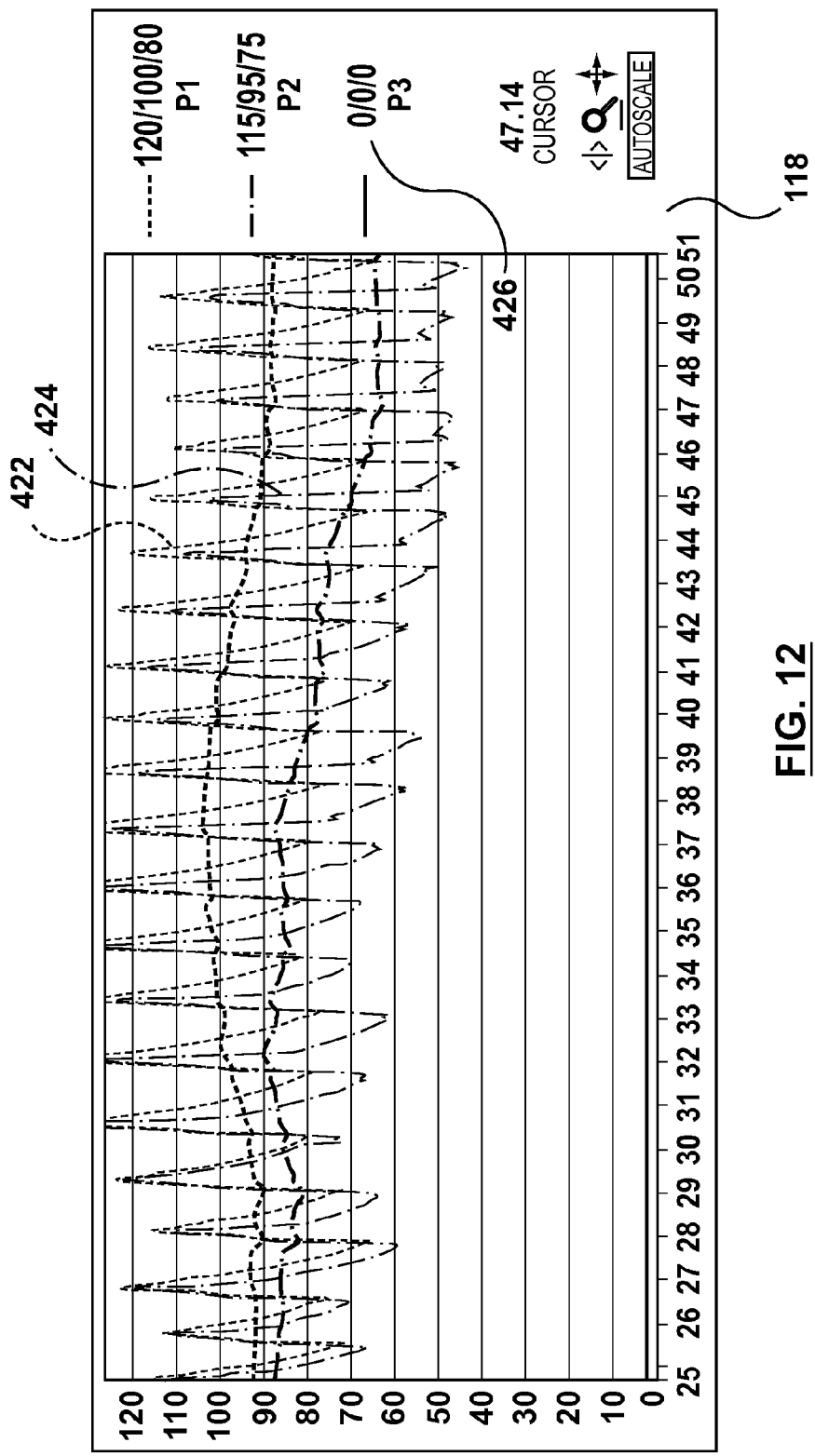

Step 318 of FIG. 7 is to insert distal pressure measurement device 122 in the patient and advance distal pressure measurement device 122 in the guide catheter of aortic pressure measurement device 124. Distal pressure measurement device 122 is generally advanced to a distal end of the guide catheter, which is where aortic pressure measurement device 124 is reading the aortic or proximal pressure. Accordingly, at this location, distal pressure measurement device 124 and aortic pressure measurement device 122 should read the same blood pressure. However, as shown in FIG. 12, the pressure trace 422 from the aortic pressure measurement device 124 and the pressure trace 424 from the distal pressure measurement device 122 often do not match up. Also, at this time, port P3 is not registering a pressure. As explained above, port P3, which is supposed to display the FFR value in pressure format, is not displaying a pressure despite port P1 (Pa) and port P2 (Pd) registering pressures. This is a safety feature that may be incorporated into controller 160 such that FFR is not outputted to hemodynamic system 110 until after the ports have been equalized.

Accordingly, aortic pressure measurement device 124 and distal pressure measurement device 122 are "equalized", as shown in step 320 of FIG. 7. This is accomplished by processing system 130 by calculating the average difference between the pressure measured by aortic pressure measurement device 124 and the pressure measured by distal pressure measurement device 122, and offsetting or applying a correction factor to the pressure measured by distal pressure measurement device 122 to equalize it with the pressure measured by aortic pressure measurement device. FIGS. 4 and 4A show an external interface 180 used to equalize the values for Pa and Pd when the distal pressure measurement device 122 and aortic pressure measurement device 124 are measuring pressure at the same location. In particular, external interface 180 may be a controller, such as an HIB controller, that is connected to controller 160 of processing unit 130. External interface 180 may be part of processing unit 130 or may be couple thereto.

Figure 13:
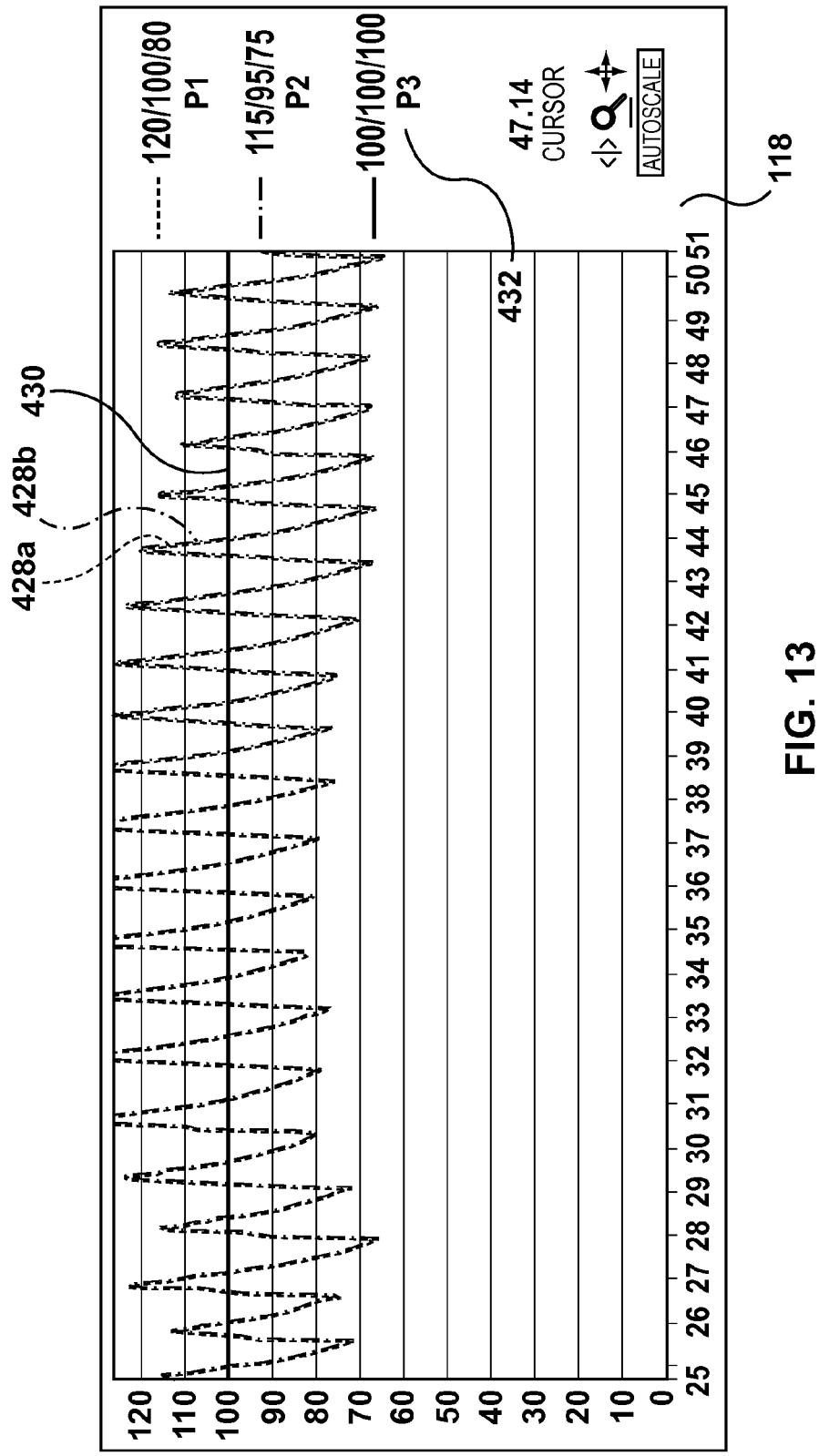

After the equalization step, with distal pressure measurement device 122 still located at the location where aortic pressure measurement device 124 takes the aortic pressure measurement (e.g., the distal end of the guide catheter), the pressure trace 428a aortic pressure measurement device 124 (Pa) and 428b for distal pressure measurement device 122 (P2) are the same, as shown in FIG. 13. Further, the pressures for both shown at 429 are the same. For clarity of visualization purposes, traces 428a/428b are shown side-by-side in FIG. 13 to represent P1 and P2. However, the traces would be nearly identical due the equalization step.

With the equalization step completed, controller 160 permits FFR to be calculated and displayed. Therefore, with distal pressure measurement device 122 still located at the location where aortic pressure measurement device 124 measures the aortic pressure, the FFR is also recorded and displayed through port P3, as explained above. Accordingly, with the distal pressure measurement device 122 and aortic pressure measurement device 122 measuring the same pressure, port P3 shows a pressure of 100 mmHg. However, as explained in detail above, while P3 displays a pressure, its value is not actually a pressure, but instead is FFR×100. Thus, as would be expected, when aortic pressure measurement device 124 and distal pressure measurement device 122 are measuring the same pressure, FFR would be 1.0. As explained above, in the embodiment where a separate scale is not used for port P3, FFR is multiplied by 100 in order to be within the same scale range as the measured pressures, and is converted to a pressure format. Thus, as shown in FIG. 13, FFR is displayed at trace 430 as 100 mmHg. However, a user knows that this trace is an FFR of 1.0. Further, P3 shows the FFR×100, as shown at 432 of FIG. 13.

With distal pressure measurement device 122 and aortic pressure measurement device 124 equalized and calibrated, distal pressure measurement device 122 is advanced into the target vessel such that distal pressure measurement device 122 measures blood pressure distal of the target lesion within the target blood vessel. For example, and not by way of limitation, a guidewire with a pressure transducer may be advanced such that the pressure transducer is located within the target blood vessel distal of the target lesion, in the direction of blood flow. In another example, and also not by way of limitation, distal pressure measurement device 122 is a catheter advanced over a guidewire, as described in co-pending U.S. application Ser. No. 14/259,896, incorporated by reference herein in its entirety above. The distal end of the catheter is advanced past the lesion such that the distal end of the catheter is located in the target blood vessel distal of the target lesion. Blood from distal of the target lesion is allowed to enter a distal opening of the catheter such that a transducer located within the catheter measures the pressure of blood distal of the target lesion. Other embodiments of distal pressure measurement device may also be used, as explained above. With distal pressure measure device 122 measuring blood pressure distal of the target lesion and aortic pressure measurement device 124 measuring blood pressure proximal of the target lesion, processing system 130 performs the steps described with respect to FIGS. 4-5 above, thereby resulting in a display such as shown on FIG. 6, with "P1" showing the aortic blood pressure ($P_a$) in mmHg, "P2" showing the distal blood pressure ($P_d$) in mmHg, and "P3" showing the FFR calculation multiplied 100 and shown in mmHg, despite FFR being unitless. Thus, a physician or other user knows that FFR for the display shown in FIG. 6, for example, is 0.71 merely by dividing P3 by 100.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment.

What is claimed is:

1. A processing system for receiving data from pressure measurement devices and communicating data to a conventional hemodynamic monitoring system having pressure displays, the processing system comprising:
   a first data input for receiving a proximal pressure measurement ($P_a$) signal from an aortic pressure measurement device;
   a second data input for receiving a distal pressure measurement ($P_d$) signal from a distal pressure measurement device;
   a controller configured to:
      compute a Fraction Flow Reserve (FFR) ratio from the proximal pressure measurement signal and the distal pressure measurement signal;
      convert the FFR ratio to a pressure format such that the FFR ratio reads on the conventional hemodynamic system as a pressure in units of pressure;
      transmit a first data output signal representing the proximal pressure measurement signal to the conventional hemodynamic monitoring system;
      transmit a second data output signal representing the distal pressure measurement signal to the conventional hemodynamic monitoring system; and
      transmit a third data output signal representing the FFR ratio in the pressure format to the conventional hemodynamic monitoring system,
   wherein the processing system is separate from the conventional hemodynamic monitoring system.

2. The processing system of claim 1, wherein the controller is further configured to scale the converted FFR ratio such that the converted FFR ratio is in a similar scale as the proximal pressure measurement and the distal pressure measurement.

3. The processing system of claim 1, further comprising a first analog-to-digital converter for converting the proximal pressure measurement signal into a proximal pressure digital signal.

4. The processing system of claim 3, further comprising a second analog-to-digital converter for converting the distal pressure measurement signal into a distal pressure digital signal.

5. The processing system of claim 4, wherein the first analog-to-digital converter and the second analog converter convert the proximal pressure measurement signal and the distal pressure measurement signal prior to the controller computing the FFR ratio.

6. The processing system of claim 5, further comprising a first digital-to-analog converter for converting the proximal pressure digital signal to the first data output signal for transmission to the conventional hemodynamic monitoring system.

7. The processing system of claim 6, further comprising a second digital-to-analog converter for converting the distal pressure digital signal to the first data output signal for transmission to the conventional hemodynamic monitoring system.

8. The processing system of claim 1, wherein the second data input comprises a wireless receiver for wirelessly receiving the distal pressure measurement signal.

9. The processing system of claim 1, wherein the second data input comprises an input jack for receiving the distal pressure measurement signal.

10. The processing system of claim 1, further comprising a wireless transmitter for wirelessly transmitting the first data output signal, the second data output signal, and the third data output signal to the conventional hemodynamic monitoring system.

11. The processing system of claim 1, wherein the pressure format is American National Standards Institute/Association for the Advancement of Medical Instrumentation (ANSI/AAMI) Blood Pressure Transducers, general (BP22)-1994 standard for blood pressure transducers.

12. A method of utilizing a conventional hemodynamic monitoring system to display data during a Fractional Flow Reserve (FFR) measurement procedure, the method comprising the steps of:
   receiving a proximal pressure measurement (Pa) signal from an aortic pressure measurement device;
   receiving a distal pressure measurement (Pd) signal from a distal pressure measurement device;
   processing the proximal pressure measurement signal and the distal pressure measurement signal to compute an FFR ratio;
   converting the FFR ratio to a pressure format such that the FFR ratio reads on the conventional hemodynamic system as a pressure in units of pressure;
   transmitting the proximal pressure measurement signal to the conventional hemodynamic monitoring system;
   transmitting the distal pressure measurement signal to the conventional hemodynamic monitoring system; and
   transmitting the FFR ratio in the pressure format to the conventional hemodynamic monitoring system.

13. The method of claim 12, further comprising steps of:
   converting the proximal pressure measurement signal from an analog signal to a proximal pressure measurement digital signal prior to the processing step; and
   converting the distal pressure measurement signal from an analog signal to a digital pressure measurement digital signal prior to the processing step.

14. The method of claim 13, further comprising the steps of:
   converting the proximal pressure measurement digital signal to a proximal pressure measurement analog output signal prior to transmitting the proximal pressure measurement analog output signal to the conventional hemodynamic monitoring system; and
   converting the distal pressure measurement digital signal to a distal pressure measurement analog output signal prior to transmitting the distal pressure measurement analog output signal to the conventional hemodynamic monitoring system.

15. The method of claim 12, wherein the distal pressure measurement signal is received from a catheter based distal pressure measurement device, further comprising the step of:
   applying a correction factor to the FFR ratio to adjust the FFR ratio to account for differences in blood flow around the catheter-based distal pressure measurement device and a wire-based distal pressure measurement device.

16. The method of claim 12, wherein the processing step further includes the steps of:
   selecting a type of distal pressure measurement device; and applying a correction factor to the FFR ratio based on the selected type of the distal pressure measurement device.

17. The method of claim 12, wherein the step of receiving the distal pressure measurement from the distal pressure measurement device comprises wirelessly receiving the distal pressure measurement from the distal pressure measurement device.

18. The method of claim 12, wherein the steps of transmitting the proximal pressure measurement signal, the distal pressure measurement signal, and the FFR ratio in pressure format to the conventional hemodynamic monitoring system comprises wirelessly transmitting the proximal pressure measurement signal, the distal pressure measurement signal, and the FFR ratio in pressure format to the conventional hemodynamic monitoring system.

19. The method of claim 12, further comprising scaling the converted FFR ratio such that the converted FFR ratio is in a similar scale as the proximal pressure measurement and the distal pressure measurement.

20. The method of claim 12, wherein the pressure format is American National Standards Institute/Association for the Advancement of Medical Instrumentation (ANSI/AAMI) Blood Pressure Transducers, general (BP22)-1994 standard for blood pressure transducers.

* * * * *